(12) United States Patent
Lynch et al.

(10) Patent No.: US 7,943,573 B2
(45) Date of Patent: May 17, 2011

(54) METHODS FOR TREATMENT OF DISTRACTION OSTEOGENESIS USING PDGF

(75) Inventors: Samuel E. Lynch, Franklin, TN (US); Charles E. Hart, Brentwood, TN (US); Michael G. Ehrlich, Providence, RI (US); Douglas C. Moore, Barrington, RI (US)

(73) Assignee: BioMimetic Therapeutics, Inc., Franklin, TN (US)

( * ) Notice: Subject to any disclaimer, the term of this patent is extended or adjusted under 35 U.S.C. 154(b) by 3 days.

(21) Appl. No.: 12/368,242

(22) Filed: Feb. 9, 2009

(65) Prior Publication Data

US 2009/0232890 A1 Sep. 17, 2009

Related U.S. Application Data

(60) Provisional application No. 61/026,934, filed on Feb. 7, 2008.

(51) Int. Cl.
*A61K 38/19* (2006.01)
*A61K 38/17* (2006.01)

(52) U.S. Cl. ....... 514/8.2; 514/16.7; 514/17.2; 424/422; 424/423; 424/444; 424/455

(58) Field of Classification Search .................. None
See application file for complete search history.

(56) References Cited

U.S. PATENT DOCUMENTS

| | | | |
|---|---|---|---|
| 3,943,072 A | 3/1976 | Thomson et al. |
| 4,845,075 A | 7/1989 | Murray et al. |
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |

(Continued)

FOREIGN PATENT DOCUMENTS

EP 0 289 584 B1 11/1988

(Continued)

OTHER PUBLICATIONS

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2F%2Fwww%2E7ware%...<, last visited on Feb. 24, 2010, 2 pages.

(Continued)

*Primary Examiner* — Elizabeth C. Kemmerer
(74) *Attorney, Agent, or Firm* — Morrison & Foerster LLP

(57) ABSTRACT

The present invention relates to compositions and methods for use in osteodistraction procedures. In one embodiment, a method of stimulating osteogenesis during and/or following bone distraction comprises providing a composition comprising a PDGF solution disposed in a biocompatible matrix and applying the composition to at least one site of bone distraction.

46 Claims, 2 Drawing Sheets

U.S. PATENT DOCUMENTS

| | | |
|---|---|---|
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,376,636 A | 12/1994 | Rutherford et al. |
| 5,457,093 A | 10/1995 | Cini et al. |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A * | 7/1996 | Moore .................. 435/384 |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,783,217 A | 7/1998 | Lee et al. |
| 5,804,176 A | 9/1998 | Grotendorst |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 * | 8/2001 | Gordon .................. 433/173 |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 * | 10/2002 | Gilbertson et al. ........ 424/198.1 |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 * | 9/2005 | Dalal et al. .................. 424/423 |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 * | 3/2007 | Gilbertson et al. ........ 424/198.1 |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 * | 2/2009 | Hart et al. .................... 424/85.1 |
| 7,597,883 B2 * | 10/2009 | Hart et al. .................... 424/85.1 |
| 7,799,754 B2 | 9/2010 | Hart et al. |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen et al. |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1 | 3/2003 | Dalal et al. |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |
| 2005/0107887 A1 | 5/2005 | Knothe Tate et al. |
| 2005/0119754 A1 | 6/2005 | Trieu et al. |
| 2005/0169893 A1 * | 8/2005 | Koblish et al. .................. 424/93.7 |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2006/0029578 A1 | 2/2006 | Hoemann et al. |

| | | | |
|---|---|---|---|
| 2006/0084602 A1 | 4/2006 | Lynch | |
| 2006/0149392 A1 | 7/2006 | Hsieh et al. | |
| 2006/0153817 A1 | 7/2006 | Kihm et al. | |
| 2006/0153818 A1 | 7/2006 | Dhanaraj et al. | |
| 2006/0154367 A1 | 7/2006 | Kihm et al. | |
| 2006/0177475 A1 | 8/2006 | Rueger et al. | |
| 2006/0190043 A1 | 8/2006 | Brighton et al. | |
| 2006/0198939 A1 | 9/2006 | Smith et al. | |
| 2006/0205652 A1 | 9/2006 | Zamora et al. | |
| 2006/0233853 A1 | 10/2006 | Remington et al. | |
| 2006/0247156 A1 | 11/2006 | Vanderby et al. | |
| 2006/0292198 A1 | 12/2006 | Dalal et al. | |
| 2007/0003752 A1 | 1/2007 | Bruce et al. | |
| 2007/0026044 A1 | 2/2007 | Bunting et al. | |
| 2007/0048381 A1 | 3/2007 | Hart et al. | |
| 2007/0053951 A1 | 3/2007 | Gonzalez Santos et al. | |
| 2007/0129807 A1 | 6/2007 | Lynch et al. | |
| 2007/0160681 A1 | 7/2007 | Park et al. | |
| 2007/0190101 A1 | 8/2007 | Yang et al. | |
| 2007/0191851 A1 | 8/2007 | Ashammakhi | |
| 2007/0207185 A1 | 9/2007 | Hart et al. | |
| 2007/0218098 A1 | 9/2007 | Reif et al. | |
| 2007/0244484 A1 | 10/2007 | Luginbuehl | |
| 2007/0259018 A1 | 11/2007 | McKay | |
| 2007/0259814 A1 | 11/2007 | Lynch | |
| 2007/0260326 A1 | 11/2007 | Williams et al. | |
| 2007/0282455 A1 | 12/2007 | Luginbuehl et al. | |
| 2008/0027470 A1 | 1/2008 | Hart et al. | |
| 2009/0074753 A1 | 3/2009 | Lynch | |
| 2009/0092674 A1 | 4/2009 | Ingram et al. | |
| 2009/0130173 A1 | 5/2009 | Behnam et al. | |
| 2010/0136085 A1 | 6/2010 | Hart et al. | |
| 2010/0151025 A1 | 6/2010 | Lynch et al. | |
| 2010/0174368 A1 | 7/2010 | Lynch et al. | |
| 2010/0183515 A1 | 7/2010 | Hart et al. | |
| 2010/0196347 A1 | 8/2010 | Kery et al. | |
| 2010/0247651 A1 | 9/2010 | Kestler et al. | |

FOREIGN PATENT DOCUMENTS

| | | | |
|---|---|---|---|
| EP | 0 479 799 B1 | 4/1992 | |
| EP | 0 530 804 A1 | 3/1993 | |
| EP | 0 530 804 B1 | 3/1993 | |
| EP | 0 741 785 B1 | 11/1996 | |
| EP | 0 741 785 B2 | 11/1996 | |
| EP | 0 896 825 A1 | 2/1999 | |
| EP | 0 896 825 B1 | 2/1999 | |
| EP | 0 994 694 B1 | 4/2000 | |
| EP | 1 025 871 A1 | 8/2000 | |
| EP | 1 100 488 B1 | 5/2001 | |
| EP | 1 146 897 B1 | 10/2001 | |
| EP | 1 234 552 A1 | 8/2002 | |
| EP | 1 234 552 B1 | 8/2002 | |
| EP | 1 242 129 B1 | 9/2002 | |
| EP | 1 374 857 A1 | 1/2004 | |
| EP | 1 410 811 A1 | 4/2004 | |
| EP | 1 410 811 B1 | 4/2004 | |
| EP | 1 464 307 A1 | 10/2004 | |
| EP | 1 464 307 B1 | 10/2004 | |
| EP | 1 561 481 A2 | 8/2005 | |
| EP | 1 561 481 A3 | 8/2005 | |
| EP | 1 563 846 A1 | 8/2005 | |
| EP | 1 681 087 A2 | 7/2006 | |
| EP | 1 681 087 A3 | 7/2006 | |
| EP | 1 712 244 A1 | 10/2006 | |
| EP | 1 719 531 A2 | 11/2006 | |
| EP | 1 719 532 A2 | 11/2006 | |
| GB | 2 367 497 A | 4/2002 | |
| JP | 7-250688 A | 10/1995 | |
| JP | 2003-265592 A | 9/2003 | |
| WO | WO-88/03409 A1 | 5/1988 | |
| WO | WO-91/15231 A1 | 10/1991 | |
| WO | WO-91/18098 A1 | 11/1991 | |
| WO | WO-92/09301 A1 | 6/1992 | |
| WO | WO-92/16181 A2 | 10/1992 | |
| WO | WO-93/00432 A1 | 1/1993 | |
| WO | WO-93/05808 A1 | 4/1993 | |
| WO | WO-93/08825 A1 | 5/1993 | |
| WO | WO-93/09229 A1 | 5/1993 | |
| WO | WO-93/16099 A2 | 8/1993 | |
| WO | WO-93/20859 A1 | 10/1993 | |
| WO | WO-94/01557 A1 | 1/1994 | |
| WO | WO-94/05800 A1 | 3/1994 | |
| WO | WO-94/15949 A1 | 7/1994 | |
| WO | WO-94/15965 A1 | 7/1994 | |
| WO | WO-94/15966 A1 | 7/1994 | |
| WO | WO-94/21681 A1 | 9/1994 | |
| WO | WO-94/22463 A1 | 10/1994 | |
| WO | WO-94/26892 A1 | 11/1994 | |
| WO | WO-94/26893 A1 | 11/1994 | |
| WO | WO-94/28889 A1 | 12/1994 | |
| WO | WO-95/01801 A1 | 1/1995 | |
| WO | WO-95/01802 A1 | 1/1995 | |
| WO | WO-95/07982 A1 | 3/1995 | |
| WO | WO-95/10539 A1 | 4/1995 | |
| WO | WO-95/16035 A2 | 6/1995 | |
| WO | WO-95/16035 A3 | 6/1995 | |
| WO | WO-95/18856 A1 | 7/1995 | |
| WO | WO-95/20967 A1 | 8/1995 | |
| WO | WO-95/28124 A2 | 10/1995 | |
| WO | WO-95/28124 A3 | 10/1995 | |
| WO | WO-95/28950 A1 | 11/1995 | |
| WO | WO-96/01845 A1 | 1/1996 | |
| WO | WO-96/02559 A1 | 2/1996 | |
| WO | WO-96/13226 A1 | 5/1996 | |
| WO | WO-96/16668 A1 | 6/1996 | |
| WO | WO-96/17924 A2 | 6/1996 | |
| WO | WO-96/17924 A3 | 6/1996 | |
| WO | WO-97/13857 A1 | 4/1997 | |
| WO | WO-98/00183 A2 | 1/1998 | |
| WO | WO-98/00183 A3 | 1/1998 | |
| WO | WO-98/40113 A1 | 9/1998 | |
| WO | WO-98/41246 A2 | 9/1998 | |
| WO | WO-98/41246 A3 | 9/1998 | |
| WO | WO-98/51354 A2 | 11/1998 | |
| WO | WO-98/51354 A3 | 11/1998 | |
| WO | WO-99/30726 A1 | 6/1999 | |
| WO | WO-99/38543 A2 | 8/1999 | |
| WO | WO-99/38543 A3 | 8/1999 | |
| WO | WO-99/67289 A1 | 12/1999 | |
| WO | WO-00/04940 A1 | 2/2000 | |
| WO | WO-01/32197 A2 | 5/2001 | |
| WO | WO-01/32197 A3 | 5/2001 | |
| WO | WO-01/35932 A2 | 5/2001 | |
| WO | WO-01/35932 A3 | 5/2001 | |
| WO | WO-01/41822 A1 | 6/2001 | |
| WO | WO-01/57083 A1 | 8/2001 | |
| WO | WO-01/60242 A3 | 8/2001 | |
| WO | WO-01/60424 A2 | 8/2001 | |
| WO | WO-01/66044 A2 | 9/2001 | |
| WO | WO-01/66044 A3 | 9/2001 | |
| WO | WO-01/66130 A1 | 9/2001 | |
| WO | WO-01/68135 A2 | 9/2001 | |
| WO | WO-01/68135 A3 | 9/2001 | |
| WO | WO-02/00244 A2 | 1/2002 | |
| WO | WO-02/00244 A3 | 1/2002 | |
| WO | WO-02/00272 A2 | 1/2002 | |
| WO | WO-02/00272 A3 | 1/2002 | |
| WO | WO-02/36147 A1 | 5/2002 | |
| WO | WO-02/062405 A2 | 8/2002 | |
| WO | WO-02/062405 A3 | 8/2002 | |
| WO | WO-02/067978 A1 | 9/2002 | |
| WO | WO-02/070029 A2 | 9/2002 | |
| WO | WO-02/070029 A3 | 9/2002 | |
| WO | WO-02/102783 A1 | 12/2002 | |
| WO | WO-03/006025 A1 | 1/2003 | |
| WO | WO-03/043576 A2 | 5/2003 | |
| WO | WO-03/043576 A3 | 5/2003 | |
| WO | WO-03/065996 A2 | 8/2003 | |
| WO | WO-03/065996 A3 | 8/2003 | |
| WO | WO-03/070186 A2 | 8/2003 | |
| WO | WO-03/070186 A3 | 8/2003 | |
| WO | WO-03/071997 A1 | 9/2003 | |
| WO | WO-2004/002539 A2 | 1/2004 | |
| WO | WO-2004/002539 A3 | 1/2004 | |
| WO | WO-2004/002539 C1 | 1/2004 | |
| WO | WO-2004/010907 A1 | 2/2004 | |
| WO | WO-2004/071543 A1 | 8/2004 | |
| WO | WO-2004/073563 A2 | 9/2004 | |

| | | |
|---|---|---|
| WO | WO-2004/073563 A3 | 9/2004 |
| WO | WO-2004/110308 A2 | 12/2004 |
| WO | WO-2004/110308 A3 | 12/2004 |
| WO | WO-2004/110308 C2 | 12/2004 |
| WO | WO-2005/009496 A1 | 2/2005 |
| WO | WO-2005/032461 A2 | 4/2005 |
| WO | WO-2005/032461 A3 | 4/2005 |
| WO | WO-2005/042048 A2 | 5/2005 |
| WO | WO-2005/042048 A3 | 5/2005 |
| WO | WO-2005/046746 A1 | 5/2005 |
| WO | WO-2005/054279 A1 | 6/2005 |
| WO | WO-2005/054279 C1 | 6/2005 |
| WO | WO-2005/072656 A1 | 8/2005 |
| WO | WO-2006/031388 A2 | 3/2006 |
| WO | WO-2006/031388 A3 | 3/2006 |
| WO | WO-2006/034365 A2 | 3/2006 |
| WO | WO-2006/034365 A3 | 3/2006 |
| WO | WO-2006/044334 A2 | 4/2006 |
| WO | WO-2006/044334 A3 | 4/2006 |
| WO | WO-2006/050493 A2 | 5/2006 |
| WO | WO-2006/050493 A3 | 5/2006 |
| WO | WO-2006/093808 A1 | 9/2006 |
| WO | WO-2006/133403 A2 | 12/2006 |
| WO | WO-2006/133403 A3 | 12/2006 |
| WO | WO-2007/061889 A2 | 5/2007 |
| WO | WO-2007/061889 A3 | 5/2007 |
| WO | WO-2007/087436 A2 | 8/2007 |
| WO | WO-2007/087436 A3 | 8/2007 |
| WO | WO-2007/089997 A2 | 8/2007 |
| WO | WO-2007/089997 A3 | 8/2007 |
| WO | WO-2007/090102 A2 | 8/2007 |
| WO | WO-2007/090102 A3 | 8/2007 |
| WO | WO-2007/092622 A2 | 8/2007 |
| WO | WO-2007/092622 A3 | 8/2007 |
| WO | WO-2008/005427 A2 | 1/2008 |
| WO | WO-2008/005427 A3 | 1/2008 |
| WO | WO-2008/073628 A2 | 6/2008 |
| WO | WO-2008/073628 A3 | 6/2008 |
| WO | WO-2008/103690 A1 | 8/2008 |
| WO | WO-2008/151193 A1 | 12/2008 |
| WO | WO-2009/100454 A1 | 8/2009 |
| WO | WO-2010/030714 A2 | 3/2010 |
| WO | WO-2010/071857 A1 | 6/2010 |
| WO | WO-2010/102266 A1 | 9/2010 |

OTHER PUBLICATIONS

Adalberto et al. "Periodontal Regeneration," *J. Periodontal*, 2005, 76(9)1 601-1622.

Adornato, M.C. et al. (Jul. 2007). "The Treatment of Bisphosphonate-Associated Osteonecrosis of the Jaws with Bone Resection and Autologous Platelet-Derived Growth Factors," *Journal of the American Dental Association* 138(7) :971 -977.

Advisory Action Before the Filing of an Appeal Brief mailed on Apr. 4, 2008, for U.S. Appl. No. 11/159,533, filed Jun. 23, 2005, 3 pages.

Advisory Action Before the Filing of an Appeal Brief mailed on Jun. 4, 2008, for U.S. Appl. No. 11/159,533, filed Jun. 23, 2005, 3 pages.

Aghaloo, T.L. DDS MD et al. "Evaluation of Platelet-Rich Plasma in Combination with Anorganic Bovine Bone in the Rabbit Cranium: A Pilot Study," *The International Journal of Oral and Maxillofacial Implants*; 2004, 19:59-65.

Ahn, S-H. et al. (Jun. 2003). "Effect of Recombinant Human Bone Morphogenetic Protein-4 with Carriers in Rat Calvarial Defects," *Journal of Periodontology* 74(6):787-797.

Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," *Tissue Eng.* 10(5/6):789-795.

Almojaly, S. (2008). "The Effect of Bisphosphonate, Alendronate, on Primary Human Alveolar Bone Cells," *Masters Abstracts International* 46(6):61.

Amendment After Request for Continued Examination submitted on Aug. 7, 2008, for U.S. Appl. No. 11/159,533, filed Jun. 23, 2005, 18 pages.

Amendment and Response to Final Office Action submitted on Feb. 25, 2008, for U.S. Appl. No. 11/159,533, filed Jun. 23, 2005, 9 pages.

Amendment and Response to Non-Final Office Action submitted on Oct. 26, 2007, for U.S. Appl. No. 11/159,533, filed Jun. 23, 2005, 15 page.

Amendment in Response to Non-Final Office Action submitted on Dec. 18, 2009, for U.S. Appl. No. 11/704,685, filed Feb. 9, 2007, 32 pages.

American Dental Association (Jun. 2006). *Expert Panel Recommendations: Dental Management of Patients on Oral Bisphosphonate Therapy, Report of the Council of Scientific Affairs*, 14 pages.

Anitua, E. et al. "Autologous platelets as a source of proteins for healing and tissue regeneration," *Thromb Haemost*, 2004, 91:4-15.

Anitua et al. (2005). "Autologous Preparations Rich in Growth Factors Promote Proliferation and Induce VEGF and HGF Production by Human Tendon Cells in Culture," *Journal of Orthopaedic Research* 23:281-286.

Anonymous (2003). "The European Market for Dental Bone Graft Substitutes," *Implant Dentistry* 12(1):3-5.

Antoniades, H.N. et al. (May 27, 1983). "Human Platelet-Derived Growth Factor (PDGF): Amino-Terminal Amino Acid Sequence," *Science* 220:963-965.

Antoniades, H.N. et al. (1985). "Platelet-Derived Growth Factor: A Link to Malignant Transformation," in *Cancer Cells 3: Growth Factors and Transformations*, Fermasico, J. et al. eds., Cold Spring Harbor Laboratory: Cold Spring Harbor, NY, 3:145-151.

Antoniades, H.N. et al. (1991). "Molecular Mechanism of Tissue Repair: Injury Induces Expression of PDGF-B and its Receptor," Abstract No. 2156, *J. Dental Res.* 70:536.

Anusaksathien et al. "Growth Factor Delivery to Re-Engineer Periodontal Tissues," *Current Pharmaceutical Biotechnology*, 2002, vol. 3(2):129-139.

Anusaksathien et al. "Platelet-Derived Growth Factor Gene Delivery Stimulates ex Vivo Gingival Repair," *Tissue Engineering*, 2003, 9(4):745-758.

Anusaksathien et al. "Effect of Sustained Gene Delivery of Platelet-Derived Growth Factor or Its Antagonist (PDGF-1308) on Tissue-Engineered Cementum," *J. Periodontal*, Mar. 2004, 75(3):429-440.

Arm, D.M. et al. "Effect of Controlled Release of Platelet-derived Growth Factor from a Porous Hydroxyapatite Implant on Bone Ingrowth," *Biomaterials*, 1996, 17(7):703-709.

Assael, L.A. (2006). "A Time for Perspective on Bisphosphonates," *J. Oral Maxillofac. Surg.* 64:877-879.

Babbush, C.A. DDS MSCD et al. "An in Vitro and in Vivo Evaluation of Autologous Platelet Concentrate in Oral Reconstruction," *Implant Dent.*, 2003, 12(1):24-34.

Barker, K. et al. (Jun. 2006). "Bisphosphonate-Associated Osteonecrosis of the Jaws: A Guide for the General Dental Practitioner," *Dental Update* pp. 270-275.

Basa, S. et al. (2004). "Alternative Bone Expansion Technique for Immediate Placement of Implants in the Edentulous Posterior Mandibular Ridge: A Clinical Report," *International Journal of Oral & Maxofacial Implants* 19(4):554-558.

Bateman, J. et al. "Platelet-Derived Growth Factor Enhancement of Two Alloplastic Bone Matrices," *J. Periodontol.* (Nov. 2005) 76(11):1833-1841.

Becker. W. et al. (Nov. 1992). "A Comparison of PTFE Membranes Alone or in Combination with Platelet-Derived Growth Factor and Insulin-Like Growth Factor-I, or Demineralized Freeze Dried Bone in Promoting Bone Formation Around Immediate Extraction Socket Implants: A Study in Dogs," *J. Periodtonol*. 63(11):929-940.

Berlemann, U. et al. (2002). "Adjacent Vertebral Failure After Vertebroplasty," *J. Bone Joint Surg. BR* 84(B):748-752.

Betsholtz, C. et al. (Apr. 24, 1986). "cDNA Sequence and Chromosomal Localization of Human Platelet-Derived Growth Factor A-Chain and its Expression In Tumour Cell Lines," *Nature* 320:695-699.

Biomimetic Therapeutics (Aug. 21, 2002). "Orthovita and BioMimetic Enter into a Supply Agreement," Located at <http://biomimetics.com/cgi-bin/aw/acuweb.cgi?s=biomimetics&t=pressreleasedtl.htm&StoryID=82&>, last visited on May 18, 2010, 6 pages.

Biomimetic Therapeutics (May 21, 2003). "BioMimetic Pharmaceuticals, Inc. Closes Series B Venture Funding," located at <http:// biomimetics.com/cgi-bin/aw/acuweb.cgi?s=biomimetics
&t=pressreleasedtl.htm&StoryID=76&>, last visited on May 18, 2010, 5 pages.
Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics &t=pressreleasedtl.htm&StoryID=83&>, last visited on May 18, 2010, 6 pages.
Biomimetic Therapeutics (Jul. 15, 2004). "BioMimetic Pharmaceuticals' Receives Approvable Recommendation from FDA Advisory Panel for *GEM 21S®*," located at <http://biomimetics.com/cgi-bin/aw/acuweb.cgi?s=biomimetics&t=pressreleasedtl.htm &StoryID=78&>, last visited on May 18, 2010, 6 pages.
Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics &t=pressreleasedtl.htm&StoryID=79&>, last visited on May 20, 2010, 5 pages.
Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics &t=pressreleasedtl.htm&StoryID=80&>, last visited on May 18, 2010, 6 pages.
Biomimetic Therapeutics (Jul. 13, 2005). "BioMimetic Pharmaceuticals Strengthens Senior Leadership Team," located at <http://biomimetics.com/cgi-bin/aw/acuwebcgi?s=biomimetics &t=pressreleasedtl.htm&StoryID=81&>, last visited on May 20, 2010, 6 pages.
Biomimetic Therapeutics (Nov. 21, 2005). "BioMimetic Therapeutics Announces FDA Approval of *GEM 21S®* Growth-Factor Enhanced Matrix for the Treatment of Periodontally-Related Bone Defects," located at <http://biomimetics.com/cgi-bin/aw/acuweb.cgi?s=biomimetics&t=pressreleasedtl.htm&StoryID=87&>, last visited on May 18, 2010, 6 pages.
Biomimetic Therapeutics (Mar. 20, 2006). "BioMimetic Therapeutics Initiates Trials with Novel Bio-Active Drug-Device Combination Bone Graft in Two Orthopedic Indications," located at <http://biomimetics.com/cgi-bin/aw/acuweb.cgi?s=biomimetics &t=pressreleasedtl.htm&StoryID=118&>, last visited on May 18, 2010, 6 pages.
Biomimetic Therapeutics (Jun. 7, 2006). "BioMimetic Therapeutics Receives Approval to Market GEM 21S® Growth-Factor Enhanced Matrix in Canada," located at <http://www.biomimetics.com/cgi-bin/acuweb/acuweb.cgi?s=biom&t=NewsDetail.htm&StoryID=166 &>, 5 pages.
Biomimetic Therapeutics (Jul. 11, 2006). "BioMimetic Therapeutics Successfully Completes Enrollment in Three Orthopedic Pilot Clinical Trials for GEM OS1™ Bone Graft; Canadian Study Expanded to 60 Patients," located at <http://biomimetics.com/cgi-bin/aw/acuweb.cgi?s=biomimetics&t=pressreleasedtl.htm&StoryID=93&>, last visited on May 18, 2010, 6 pages.
Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at <http://biomimetics.com/cgi-bin/aw/acuweb.cgi?s=biomimetics &t=pressreleasedtl.htm&StoryID=94&>, last visited on May 18, 2010, 6 pages.
Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics &t=pressreleasedtl.htm&StoryID=97&>, last visited on May 20, 2010, 6 pages.
Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressreleasedtl.htm&StoryID=101 &>, last visited on May 18, 2010, 7 pages.
Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb.cgi?s=biomimetics&t=pressreleasedtl.htm &StoryID=104&>, last visited on May 18, 2010, 7 pages.

Biomimetic Therapeutics (Jan. 25, 2007). "BioMimetic Therapeutics Reports Positive Clinical Results Using *GEM OS ®* to Treat Distal Radius Fractures," located at <http://biomimetics.com/cgi-bin/aw/acuweb.cgi?s=biomimetics&t=pressreleasedtl.htm&StoryID=105 &>, last visited on May 18, 2010, 6 pages.
Biomimetic Therapeutics (Feb. 21, 2007). "BioMimetic Therapeutics Receives Orphan Drug Designation for rhPDGF-BB Treatment of Osteonecrosis of the Jaw," located at < http://biomimetics.com/cgi-bin/aw/acuweb.cgi?s=biomimetics&t=pressreleasedtl.htm &StoryID=112&>, last visited on Apr. 5, 2010, 6 pages.
Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at <http://biomimetics.com/cgi-bin/aw/acuweb.cgi?s=biomimetics&t=pressreleasedtl.htm&StoryID=113&>, last visited on May 18, 2010, 8 pages.
Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressreleasedtl.htm&StoryID=111&>, last visited on May 18, 2010, 4 pages.
Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressreleasedtl.htm &StoryID=116&>, last visited on May 18, 2010, 7 pages.
Biomimetic Therapeutics (Jun. 7, 2007). "BioMimetic Therapeutics Initiates Enrollment in E.U. Registration Trial for GEM OS®1 Bone Graft; U.S. GEM OS1 Pivotal Study Protocol Amended to Allow Shorter Follow-Up Time and More Patients," located at <http://biomimetics.com/cgi-bin/aw/acuweb.cgi?s=biomimetics &t=pressreleasedtl.htm&StoryID=119&>, last visited on May 18, 2010, 6 pages.
Biomimetic Therapeutics (Jul. 13, 2007). "BioMimetic Therapeutics' Clinical Investigator Presents Positive Interim Data on U.S. and Canadian Foot and Ankle Clinical Trials," located at <http://biomimetics.com/cgi-bin/aw/acuweb.cgi?s=biomimetics &t=pressreleasedtl.htm&StoryID=123&>, last visited on May 18, 2010, 8 pages.
Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics &t=pressreleasedtl.htm&StoryID=125&>, last visited on May 18, 2010, 7 pages.
Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics &t=pressreleasedtl.htm&StoryID=127&>, last visited on May 18, 2010, 7 pages.
Biomimetic Therapeutics (Dec. 13, 2007). "BioMimetic Therapeutics reports Positive Clinical Results for GEM OS®1 in Canadian Foot and Ankle Fusion Study; Clinical Success Rate of 90% Achieved in High Risk Patient Population," located at <http://biomimetics.com/cgi-bin/aw/acuweb.cgi?s=biomimetics &t=pressreleasedtl.htm&StoryID=131&>, last visited on May 18, 2010, 6 pages.
Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at <http://biomimetics.com/cgi-bin/aw/acuweb.cgi?s=biomimetics&t=pressreleasedtl.htm &StoryID=149&>, last visited on May 18, 2010, 7 pages.
Biomimetic Therapeutics (Feb. 29, 2008). "BioMimetic Therapeutics, Inc. to Highlight Clinical and Preclinical Activities at ORS and AAOS Meetings," located at http://biomimetics.com/cgi-bin/aw/acuweb.cgi?s=biomimetics&t=pressreleasedtl.htm&StoryID=136 &>, last visited on May 18, 2010, 6 pages.
Biomimetic Therapeutics (Mar. 7, 2008). "BioMimetic Therapeutics, Inc. Provides Updates on Clinical and Preclinical Activities; Company Receives Go Ahead from Health Canada to File GEM OS1 DLA," located at <http://biomimetics.com/cgi-bin/aw/acuweb.cgi?s=biomimetics&t=pressreleasedtl.htm&StoryID=138&>, last visited on May 18, 2010, 6 pages.

Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at <http://biomimetics.com/cgi-bin/aw/acuweb.cgi?s=biomimetics&t=pressreleasedtl.htm&StoryID=137&>, last visited on May 18, 2010, 8 pages.

Biomimetic Therapeutics (Aug. 11, 2008). "BioMimetic Therapeutics Reports 2008 Second Quarter Results; Positive Results Achieved with Augment™ Injectable Bone Graft to Enhance Healing in Foot and Ankle Fusions," located at <http://biomimetics.com/cgi-bin/aw/acuweb.cgi?s=biomimetics&t=pressreleasedtl.htm&StoryID=151&>, last visited on May 18, 2010, 8 pages.

Biomimetic Therapeutics (Sep. 23, 2008). "BioMimetic Therapeutics Announces No Changes Requested by Independent Data Monitoring Committee to Pivotal Trial Design for Augment™ Bone Graft; 268 of 396 Patients Enrolled to Date in U.S. Pivotal Trial," located at <http://biomimetics.com/cgi-bin/aw/acuweb.cgi?s=biomimetics&t=pressreleasedtl.htm&StoryID=153&>, last visited on May 18, 2010, 7 pages.

Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396 Patients Enrolled," located at <http://biomimetics.com/cgi-bin/aw/acuweb.cgi?s=biomimetics&t=pressreleasedtl.htm&StoryID=159&>, last visited on May 18, 2010, 6 pages.

Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressreleasedtl.htm&StoryID=157&>, last visited on May 18, 2010, 8 pages.

Biomimetic Therapeutics (Nov. 21, 2008). "BioMimetic Therapeutics, Inc. Announces Patent Allowance from the United Stats Patent and Trademark Office for PDGF Compositions Patent; Expanded Protection for Augment™, Augment™ Injectable and GEM 21S® Until 2024," located at <http://biomimetics.com/cgi-bin/aw/acuweb.cgi?s=biomimetics&t=pressreleasedtl.htm&StoryID=163&>, last visited on May 18, 2010, 5 pages.

Biomimetic Therapeutics (Dec. 11, 2008). "BioMimetic Therapeutics, Inc. Achieves Patient Enrollment Target (396) in North American Pivotal Study for Augment™ Bone Graft," located at <http://biomimetics.com/cgi-bin/aw/acuweb.cgi?s=biomimetics&t=pressreleasedtl.htm&StoryID=169&>, last visited on May 18, 2010, 5 pages.

Biomimetic Therapeutics (Jan. 7, 2009). "BioMimetic Therapeutics, Inc. Closes Enrollment with 436 Patients in North American Pivotal Study for Augment™ Bone Graft; Company Will File Modular PMA with the FDA Beginning This Spring," located at <http://biomimetics.com/cgi-bin/aw/acuweb.cgi?s=biomimetics&t=pressreleasedtl.htm&StoryID=168&>, last visited on May 18, 2010, 5 pages.

Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at <http://biomimetics.com/cgi-bin/aw/acuweb.cgi?s=biomimetics&t=pressreleasedtl.htm&StoryID=154&>, last visited on May 18, 2010, 6 pages.

Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressreleasedtl.htm&StoryID=160&>, last visited on May 18, 2010, 11 pages.

Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressreleasedtl.htm&StoryID=167&>, last visited on May 18, 2010, 8 pages.

Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressreleasedtl.htm&StoryID=185&>, last visited on May 18, 2010, 8 pages.

Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at < http://biomimetics.com/cgi-bin/aw/acuweb.cgi?s=biomimetics&t=pressreleasedtl.htm&StoryID=188&>, last visited on May 18, 2010, 8 pages.

Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressreleasedtl.htm&StoryID=190&>, last visited on May 18, 2010, 6 pages.

Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at <http://biomimetics.com/cgi-bin/aw/acuweb.cgi?s=biomimetics&t=pressreleasedtl.htm&StoryID=191&>, last visited on May 18, 2010, 8 pages.

Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressreleasedtl.htm&StoryID=199&>, last visited on May 18, 2010, 5 pages.

Biomimetic Therapeutics (Mar. 4, 2010). "BioMimetic Therapeutics, Inc. To Highlight Pre-Clinical and Clinical Activities at ORS and AAOS Meetings; Company to Host Analyst and Investor Meeting on Mar. 11," located at <http://biomimetics.com/cgi-bin/aw/acuweb.cgi?s=biomimetics&t=pressreleasedtl.htm&StoryID=201&>, last visited on May 18, 2010, 6 pages.

Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressreleasedtl.htm&StoryID=202&>, last visited on May 18, 2010, 6 pages.

Biomimetic Therapeutics (Mar. 11, 2010). "BioMimetic Therapeutics Reports 2009 Fourth Quarter and Year End Earnings Results; Company Releases Additional Pivotal Data on Augment," located at <http://biomimetics.com/cgi-bin/aw/acuweb.cgi?s=biomimetics&t=pressreleasedtl.htm&StoryID=203&>, last visited on May 18, 2010, 11 pages.

Biomimetic Therapeutics (Mar. 12, 2010). "Morningstar® Document ResearchSM Form 10-K," United States Securities and Exchange Commission Annual Report, located at <http://investor.biomimetics.com/phoenix.zhtml?c=196896&p=irol-sec>, last visited on May 19, 2010, 247 pages.

Björkenheim, J.M. (1989). "Structure and Function of the Rabbit's Supraspinatus Muscle After Resection of its Tendon," *Acta Orthop. Scand.* 60(4):461-463.

Boileau, P. et al. (Jun. 2005). "Arthroscopic Repair of Full-Thickness Tears of the Supraspinatus: Does the Tendon Really Heal?" *J. Bone Joint Surg. Am.* 87-A(6):1229-1240.

Bolander, "Regulation of Fracture Repair by Growth Factors," *P.S.E.B.M.*, 1992, 200:165-170.

Bonfini, T. et al. (Jan. 1, 2006). "Autologous Marrow and Platel Gel in Bone Tissue Regeneration," *Cytotherapy* 8(1), Abstract No. 239, 2 pages.

Bora, F.W. Jr. et al. (Aug. 1987). "Joint Physiology, Cartilage Metabolism, and the Etiology of Osteoarthritis," *Hand Clin.* 3(3):325-336.

Boyden, E.M. et al. (Aug. 1995). "Late Versus Early Repair of Achilles Tendon Rupture: Clinical and Biomechanical Evaluation," *Clin. Orthop. Relat. Res.* 317:150-158.

Braddock, M. et al. (Oct. 2001). "Born Again Bone: Tissue Engineering for Bone Repair," *News Physiool. Sci.* 16:208-213.

Buser, D. et al. (1991). "Effects of Growth Factors on Bone Regeneration Around Titanium Implants," Abstract No. 282, *J. Dental Res.* 70:301.

Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at <http://www.highbeam.com/doc/1G1-68027113.html>, last visited on Apr. 26, 2010, 3 pages.

Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3 pages.

Camargo et al. "Platelet-rich Plasma and Bovine Porous Bone Mineral Combined with Guided Tissue Regeneration in the Treatment of Intrabony Defects in Humans," *J Periodont Res* 2002, 37:300-306.

Camargo, L.V. PM et al. "Effectiveness of a Combination of Platelet-Rich Plasma, Bovine Porous Bone Mineral and Guided Tissue Regeneration in the Treatment of Mandibular Grade II Molar Furcations in Humans," *J. Clin. Periodontol*, 2003, 30:746-751.

Camelo et al. "Clinical, radiographic, and histologic evaluation of human periodontal defects treated with bio-oss and bio-guide," *International Journal of Periodontics and Restorative Dentistry*, 1998, 18(4):321-332.

Camelo et al. "Periodontal regeneration with an autogenous bone-bio-oss composite graft and a bio-guide membrane," *International Journal of Periodontics and Restorative Dentistry*. 2001, 21 (2):109-120.

Camelo, M. et al. (Nov. 3, 2003). "Periodontal Regeneration in Human Class II Furcations Using Purified Recombinant Human Platelet-Derived Growth Factor-BB (rhPDGF-BB) with Bone Allograft," *International Journal of Periodontics & Restorative Dentistry* 23(3):213-225.

Canalis, "Effect of Growth Factors on Bone Cell Replication and Differentiation," *Clinical Orthopedics and Related Research*, Mar. 1985, 193:246-263.

Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," *J. Periodontol*. 71(1):1743-1749.

Catalano, L. et al. (2006). "Bisphoshonates and Risk of Osteonecorisis of the Jaws," *Haema* 9(3):410-414.

Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," *Acta Orthop. Scand.* 74(5):559-564.

Cenni, E. et al. (2005, e-pub. Feb. 1, 2005). "Plasma Levels of Platelet-Derived Growth Factor BB and Transforming Growth Factor in Patients with Failed Hip Protheses," *Acta Orthopaedica* 76(1):64-66.

Chen et al. "Adenoviral Gene Transfer of PDGF Downregulates *Gas* Gene Product PDGFR and Prolongs ERK and AktIPKB Activation," *Am J Physiol Cell Physiol.*, Mar. 2002, 282:C538-0544.

Chiandussi, S. et al. (2006). "Clinical and Diagnostic Imaging of Bisphosphonate-Associated Osteonecrosis of the Jaws," *Dentomaxillofacial Radiology* 35:236-243.

Chin, M. (1995). "Distraction Osteogenesis in Maxillofacial Surgery," Chapter 9 in *Tissue Engineering: Applications in Maxillofacial Surgery and Periodontics*, Lynch, S.E. et al. eds., Quintessence Publishing, pp. 147-159.

Cho et al. (Jun. 1995). "Platelet Derived Growth Factor—Modulated Guided Tissue Regenerative Therapy," *J. Periodontol*. 66(6):522-530.

Clergeau, L.P. et al. (Feb. 1996). "Healing Response to Anorganic Bone Implantation in Periodontal Intrabony Defects in Dogs Part 1. Bone Regeneration. A Microradiographic Study," *J. Periodontool*. 67(2):140-149.

Cochran et al. "Effects of Platelet-Derived Growth Factor Isoforms on Calcium Release From Neonatal Mouse Calvariae," *Bone*, 1993, 14:53-58.

Coleman, S.H. et al. (Dec. 2003). "Chronic Rotator Cuff Injury and Repair Model in Sheep," *The Journal of Bone and Joint Surgery* 85-A(12):2391-2402.

Collins, T. et al. (Aug. 22, 1985). "Cultured Human Endothelial Cells Express Platelet-Derived Growth Factor B Chain: cDNA Cloning and Structural Analysis," *Nature* 316:748-750.

Convery, F.R. et al. (Jan.-Feb. 1972). "The Repair of Large Osteochondral Defects. An Experimental Study in Horses," *Clin. Orthop. Relat. Res*. 82:253-262.

Cooke et al. "Effect of rhPDGR-BB Delivery on Mediators of Periodontal Wound Repair," *Tissue Engineering*, 2006, 12(6):1441-1450.

Cossolin, G.S.I. et al. (Date Unknown) "Treatment of Avascular Osteonecrosis of the Jaws in Cancer Patients with a Histroy of Bisphosphonate Therapy by Combining Bone Resection and Autologous Platelet-Rich Plasma," *Hospital Santa Catarina* 10 pages.

Costa, M.A. et al. (Jul. 2006). "Tissue Engineering of Flexor Tendons: Optimization of Tenocyte Proliferation Using Growth Factor Supplementation," *Tissue Eng*. 12(7):1937-1943.

Courneya, J-P. et al. (2010). "Normal and Diseased Primary Human Tenocytes in Response to rhPDGF-BB," Poster No. 1118, 56th *Annual Meeting of the Orhopaedic Research Society*, located at < http://www.ors.org/web/Transactions/56/1118.pdf>, last visited on Feb. 23, 2010, 1 page.

Creaney, L. et al. (May 2008, e-pub. Nov. 5, 2007). "Growth Factor Delivery Methods in the Management of Sports Injuries: The State of Play," *Br. J. Sports Med*. 42(5):314-320, Abstract Only.

Curi et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," *Journal of Oral and Maxillofacial Surgery* 65(2):349-355.

Dalla-Favera, R. et al. (Nov. 12, 1982). "Chromosomal Localization of the Human Homolog (*c-sis*) of the Simian Sarcoma Virus *onc* Gene," *Science* 218:686-688.

Daniels, T.R. et al. (2008). "Application of rhPDGF-BB in Foot and Ankle Fusion Procedures," Chapter 19 in *Tissue Engineering: Applications in Maxillofacial Surgery and Periodontics*, Second Edition, Lynch, S.E. et al. eds., Quintessence Publishing Co.: Hanover Park, IL, pp. 267-275.

Donnelly, B.P. et al. (Jul. 2006). "Nucleotide Structure of Equine Platelet-Derived Growth Factor-A and-B and Expression in Horses with Induced Acute Tendinitis," *Am. J. Vet. Res*. 67(7):1218-1225, Abstract Only.

Doolittle et al. (Jul. 15, 1983). "Simian Sarcoma Virus *onc* Gene *v-sis*, Is Derived from the Gene (or Genes) Encoding a Platelet-Derived Growth Factor," *Science* 221:275-277.

Duffy, F.J. et al. (Jul. 1995). "Growth Factors and Canine Flexor Tendon Healing: Initial Studies in Uninjured and Repair Models," *The Journal of Hand Surgery* 20A(4):645-649.

Dunn, C.A. et al. (Feb. 2005, e-pub. Nov. 6, 2004). "BMP Gene Delivery for Alveolar Bone Engineering at Dental Implant Defects," *Molecular Therapy* 11(2):294-299.

Easley, M.E. et al. (May 2000). "Isolated Subtalar Arthodesis," *JBJS* 82-A(5):613-624.

Eastell, R. et al. (Mar. 1991). "Classification of Vertebral Fractures," *J. Bone Miner. Res*. 6(3):207-215.

Fagan, M.C. et al. (2008). "Simultaneous Augmentation of Hard and Soft Tissues for Implant Site Preparation Using Recombinant Human Platelet-Derived Growth Factor: A Human Case Report," *Int. J. Periodontics Restorative Dent*. 28(1):37-43.

Farrugia, M.C. et al. (Jan. 2006). "Osteonecrosis of the Mandible or Maxilla Associated with the Use of New Generation Bisphosphonates," *The Laryngoscope* 116:115-120.

Feldman, D. et al. (Sep. 1998). "In a Time of Change, Orthopedics Sector is Marked by New Modalities," *The BBI Newsletter*, located at <http://findarticles.com/p/articles/mi_m3570/is_n9_v21/ai_n27541529>, last visited on Mar. 12, 2009, 2 pages.

Fennis et al. "Mandibular reconstruction: A clinical and radiographic animal study on the use of autogenous scaffolds and platelet-rich plasma," *Int. J. Oral Maxillofac. Surg.*, 2002, 31:281-286.

Fennis et al. "Mandibular reconstruction: A histological and histomorphometric study on the use of autoge-us scaffolds, particulate cortico-cancellous bone grafts and platelet rich plasma in goats," *Int. J. Oral Maxillofac. Surg.*, 2004, 33:48-55.

Ficarra, G. et al. (2005). "Osteonecrosis of the Jaws in Periodontal Patients with a History of Bisphophonates Treatment," *J. Clin. Periodontol*. 32:1123-1128.

Final Office Action mailed on Feb. 7, 2008, for U.S. Appl. No. 11/159,533, filed Jun. 23, 2005, 8 pages.

Finkelman, R.D. et al. (1995). "Systematic PDGF ± Alendronate Increases Bone Density in OVX Rats," Abstract No. 1281, *J. Dental Res*. 74:172.

Fontana et al. "Effect of Platelet-Rich Plasma on the Pert-implant Bone Response: An Experimental Study," *Implant Dentistry*, 2004, 13:73-78.

Franco, B. et al. (Jan.-Jun. 2008). "Tissue Engineering Approaches for the Construction of a Completely Autologous Tendon Substitute," *Indian J. Plast. Surg*. 41(1):38-46, 13 pages.

Freedonia (Sep. 2006). "Biocompatible Materials. US Industry Study with Forecasts to 2010 & 2015," Study #2111, located at < http://www.freedoniagroup.com/pdf/2111smwe.pdf>, last visited on Jun. 17, 2010, 8 pages. (Table of Contents Only.).

Fribourg, D. et al. (Oct. 15, 2004). "Incidence of Subsequent Vertebral Fracture After Kyphoplasty," *Spine* 29(20):2270-2276.

Fukui, a. et al. (Sep. 1993). "Isolation and Characterization of Xenopus activin and Follistatin," *Devel. Biol.* 159(1):131-139.

Galatz, L.M. et al. (Feb. 2004). "The Outcome and Repair Integrity of Completely Arthoscopically Repaired Large and Massive Rotator Cuff Tears," *J. Bone Joint Surg. Am.* 86A(2):219-244.

Gamradt, S.C. et al. (Mar. 2007). "Platelet Rich Plasma in Rotator Cuff Repair," *Tech. In Orthop.* 22(1):26-33.

Garg, A.K. (1995). "Grafting Materials in Repair and Restoration," Chapter 5 in *Tissue Engineering: Applications in Maxillofacial Surgery and Periodontics*, Lynch, S.E. et al. eds., Quintessence Publishing, pp. 83-101.

Garg, "The Use of Platelet-Rich Plasma to Enhance the Success of Bone Grafts Around Dental Implants," *Dental Implantology Update*, Mar. 2000, 11(3):17-21.

Gazielly, D.F. et al. (Jul. 1994). "Functional and Anatomical Results After Rotator Cuff Repair," *Clin. Orthop. Relat. Res.* 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An in vivo Biomechanic Study at 3 Weeks in Canines," *J. Hand Surg. Am.* 32(3):373-379, Abstract Only.

Gerber, C. et al. (May 1994). "Mechanical Strength of Repairs of the Rotator Cuff," *J. Bone Joint Surg. Br.* 76-B(3):371-380.

Gerber, C. et al. (Apr. 2000). "The Results of Repair of Massive Tears of the Rotator Cuff," *J. Bone Joint Surg. Am.* 82-A(4):505-515.

Giannobile, W.V. et al. (1994). "Synergistic Effects of Insulin-Like Growth Factors-I (IGF-I) with Other Growth Factors on Bone Formation in vitro," Abstract No. 831, *J. Dental Res.* 73:205.

Giannobile et al. "Comparison of Canine and Non-Human Primate Animal Models for Periodontal Regenerative Therapy: Results Following a Single Administration of PDGF/IGF-I," *J. Periodontol.*, Dec. 1994, 65(12):1158-1168.

Giannobile, W.V. et al. (Nov. 1995). "Platelet Derived Growth Factor (PDGF) and Insulin-Like Growth Factor (IGF-I) Enhances Periodontal Regeneration in Macaca fascicularis," Abstract No. 28, *Advanced Dental Research* 9(3 Suppl.):29.

Giannobile, W.V. et al. (Jul. 1996). "Comparative Effects of Platelet-Derived Growth Factor and Insulin-Like Growth Factor-I, Individually and in Combination, on Periodontal Regeneration in *Macaca fascicularis*," *J. Periodontal Res.* 31(5):301-312.

Giannobile et al. "Periodontal Tissue Engineering by Growth Factors," *Bone*, Jul. 1996, 19(1), Supplement: 23S-37S.

Giannobile et al. "Non-Coordinate Control of Bone Formation Displayed by Growth Factor Combinations with IGF-I," *J Dent Res*, Sep. 1997, 76(9):1569-1578.

Giannobile et al. "Recombinant Human Osteogenic Protein-1 (OP-1) Stimulates Periodontal Wound Healing in Class III Furcation Defects," *J Periodontol*, Feb. 1998, 69(2):129-137.

Giannobile, "Platelet-Derived Growth Factor (PDGF) Gene Delivery for Application in Periodontal Tissue Engineering," *J Periodontol*, Jun. 2001, 72(6):815-823.

Giannobile, W.V. (2008). "Advances in Gene Therapy for Periodontal Bioengineering," Chapter 3 in *Tissue Engineering: Applications in Maxillofacial Surgery and Periodontics*, Second Edition, Lynch, S.E. et al. eds., Quintessence Publishing Co.: Hanover Park, IL, pp. 37-46.

Gilbertson et al. "Platelet-derived Growth Factor C (PDGF-C), a Novel Growth Factor That Binds to PDGF α and β Receptor," *The Journal of Biological Chemistry*, Jul. 20, 2001, 276(29):27406-27414.

Goutallier, D. et al. (Jul. 1994). "Fatty Muscle Degeneration in Cuff Ruptures: Pre- and Postoperative Evaluation by CT Scan," *Clin. Orthop.* 304:78-83.

Grageda, "Platelet-Rich Plasma and Bone Graft Materials: A Review and a Standardized Research Protocol," *Implant Dentistry*, 2004, 13(4):301-309.

Green et al. "Immunolocalization of platelet-derived growth factor A and B chains and PDGF-α and β-receptors in human gingival wounds," *Journal of Periodontal Research*, 1997, 32(2):209-214.

Gronwald et al. "Cloning and expression of a cDNA coding for the human platelet-derived growth factor receptor: Evidence for more than one receptor class," *Proc. Natl. Acad. Sci. USA*, May 1988, 85:3435-3439.

Hanel, D.P. et al. (Jan. 2002). "Wrist Fractures," *Orthop. Clin. North Am.* 33(1):35-57.

Harryman, D.T. et al. (Aug. 1991). "Repairs of the Rotator Cuff," *J. Bone Joint Surg. Am.* 73-A(7):982-989.

Hart et al. "Synthesis, Phosphorylation, and Degradation of Multiple Forms of the Platelet-derived Growth Factor Receptor Studied Using a Mo-clonal Antibody," *The Journal of Biological Chemistry*, Aug. 5, 1987, 262(22):10780-10785.

Hart et al. "Two Classes of PDGF Receptor Recognize Different Isoforms of PDGF," *Science*, Jun. 1988, 240:1529-1531.

Hart, C.E. et al. "Purification of PDGF-AB and PDGF-BB from Human Platelet Extracts and Identification of All Three PDGF Dimers in Human Platelets," *Biochemistry*, Jan. 9, 1990, 29(1):166-172.

Hattrup, S.J. et al. (1985). "A Review of Ruptures of the Achilles Tendon," *Foot & Ankle* 6(1):34-38.

Hee et al. (2003). "Do Autologous Growth Factors Enhance Transformational Lumbar Interbody Fusion?" *Eur. Spine. J.* 12(4):400-407.

Heini, P.F. et al. (2001, e-pub. Jun. 14, 2001). "Bone Substitutes in Vertebroplasty," *Eur. Spine J.* 10:S205-S213.

Helm et al. (Apr. 2001). "Bone Graft Substitutes for the Promotion of Spinal Arthrodesis," *Neurosur. Foc.* 10(4):1-5.

Higashi, T. et al. (Jun. 1996). "Influence of Particle Size of Calcium Phosphate Ceramics as a Capping Agent on the Formation of a Hard Tissue Barrier in Amputated Dental Pulp," *Journal of Endodontics* 22(6):281-283.

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," *Int. Orthop.* 31(6):791-797.

Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," *J. Orthopedic Res.* 26:83-90.

Hollinger, J.O. et al. (Feb. 2008). "Recombinant Human Platelet Derived Growth Factor: Biology and Clinical Applications," *J. Bone & Joint Surgery* 90-A(Suppl. 1):48-54.

Hollinger, J.O. et al. (2008). "Therapeutic Opportunities for Bone Grafting," Chapter 68 in *Principles of Regenerative Medicine*, Atala, A. et al. eds., Academic Press: Burlington, MA, pp. 1164-1175.

Hollinger, J.O. et al. (2008). "Protein Therapeutics and Bone Healing," Chapter 1 in *Tissue Engineering: Applications in Maxillofacial Surgery and Periodontics*, Second Editions, Lynch, S.E. et al. eds., Quintessence Publishing Co.: Hanover Park, IL, pp. 3-25.

Hossain, M.Z. et al. (Jul. 1996). "Biological Responses of Autogenous Bone and Beta-Tricalcium Phosphate Ceramics Transplanted into Bone Defects to Orthodontic Forces," *Cleft Palate-Craniofacial Journal* 33(4):277-283.

Howell, T.H. et al. (1996). "Polypeptide Growth Factors for Periodontal Regeneration," *Current Opinion in Periodontology* 3:149-156.

Howell et al. "A Phase I/II Clinical Trial to Evaluate a Combination of Recombinant Human Platelet-Derived Growth Factor-BB and Recombinant Human Insulin-Like Growth Factor-I in Patients with Period. Dis.," *J. Periodontol.*, Dec. 1997, 68(12):1186-1193.

Howes et al. "Platelet-Derived Growth Factor Enhances Demineralized Bone Matrix-Induced Cartilage and Bone Formation," *Calcif Tissue Int.*, 1988, 42:34-38.

Huang, L-H. et al. "The Effect of Platelet-Rich Plasma on the Coronally Advanced Flap Root Coverage Procedure: A Pilot Human Trial," J. Periodontal, Oct. 2005, 76(10)1 768-1777.

Hsu et al. (Jul. 2004). "Clinical Implications of Growth Factors in Flexor Tendon Wound Healing," *The Journal of Hand Surgery* 29A(4):551-563.

Ikezawa et al. "Characterization of Cementum Derived Growth Factor as an Insulin-Like Growth Factor-I Like Molecule," *Connective Tissue Research*, 1997, 36(4):309-319.
International Search Report mailed on Aug. 3, 2007, for PCT Application No. PCT/US2007/003582, filed on Feb. 9, 2007, 2 pages.
International Search Report mailed on Oct. 2, 2007, for PCT Application No. PCT/US05/36447, filed on Oct. 12, 2005, 1 page.
International Search Report mailed on Dec. 7, 2007, for PCT Application No. PCT/US2006/044766, filed on Nov. 17, 2006, 4 pages.
International Search Report mailed on May 20, 2009, for PCT Application No. PCT/US2007/083638, filed on Nov. 5, 2007, 5 pages.
International Search Report mailed on Jul. 8, 2009, for PCT Application No. PCT/US2008/054354, filed on Feb. 20, 2008, 8 pages.
International Search Report mailed on Aug. 4, 2008 for PCT Patent Application No. PCT/US2008/065666, filed on Jun. 3, 2008, 3 pages.
International Search Report mailed on Jun. 26, 2009, for PCT Application No. PCT/US2009/033596, filed on Feb. 9, 2009, 6 pages.
Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," *J. Biomed. Mater. Res.* 69A:454-461.
Jensen et al. "Platelet rich plasma and fresh frozen bone allograft as enhancement of implant fixation—An experimental study in dogs," *Journal of Orthopaedic Research*, 2004, 22:653-658.
Jensen, O.T. et al. (2008). "Alveolar Distraction Osteogenesis and Tissue Engineering," Chapter 14 in *Tissue Engineering: Applications in Maxillofacial Surgery and Periodontics*, Second Edition, Lynch, S.E. et al. eds., Quintessence Publishing Co.: Hanover Park, IL, pp. 203-219.
Jensen, O.T. (2008). "Dentoalveolar Modification with an Osteoperiosteal Flap and rhPDGF-BB," Chapter 15 in *Tissue Engineering: Applications in Maxillofacial Surgery and Periodontics*, Second Edition, Lynch, S.E. et al. eds., Quintessence Publishing Co.: Hanover Park, IL, pp. 220-225.
Jiang, D. et al. "Modification of an Osteoconductive Anorganic Bovine Bone Miami Matrix with Growth Factors," *J. Periodonlol.*, Aug. 1999, 70(8):834-839.
Jin et al. "Engineering of Tooth-Supporting Structures by Delivery of PDGF Gene Therapy Vectors," *Molecular Therapy*, Apr. 2004, 9(4):519-526.
Jin, Q. et al. (Mar. 5, 2008). "Nanofibrous Scaffolds Incorporating PDGF-BB Microspheres Induce Chemokine Expression and Tissue Neogenesis in Vivo," *PLoS ONE* 3(3):e1729, pp. 1-9.
Jones et al. (1992). "Isolation of Vgr-2, a Novel Member of the Transforming Growth Factor-Beta-related Gene Family," *Mol Endocnnol.* 6(11):1961-1968.
Jozsa, L. et al. (Aug. 1989). "Fibronectin and Laminin in Achilles Tendon," *Acta Orthop Sacninavica* 60(4):469-471.
Kademani, D. et al. (Aug. 2006). "Primary Surgical Therapy for Osteonecrosis of the Jaw Secondary to Bisphosphonate Therapy," *Mayo Clin. Proc.* 81(8):1100-1103.
Kaigler, "Growth factor delivery for oral and periodontal tissue engineering," *Expert Opin Drug Deliv.*, 2006, 3(5):647-662.
Kapuściński, P. et al. (Jul.-Sep. 1996). "An Analgesic Effect of Synthetic Human Calcitonin in Patients with Primary Osteoporosis," *The Polish Journal of Medicine and Pharmacy* 28(98):83-86.
Kassolis et al. "Alveolar Ridge and Sinus Augmentation Utilizing Platelet-Rich Plasma in Combination with Freeze-Dried Bone Allograft: Case Series," *Journal of Periodontology*, Oct. 2000, 71(10):1654-1661.
Kazlauskas et al. "Different effects of homo- and heterodimers of platelet-derived growth factor A and 8 chains on human and mouse fibroblasts," The EMBO Journal (1988) 7 (12):3727-3735.
Kim et al. "A Comparative Study of Osseointegration of Avana Implants in a Demineralized Freeze-Dried Bone Alone or With Platelet-Rich Plasma," *J Oral Maxillofac Surg*, 2002, 60:1018-1025.
Kim et al. "Use of Particulate Dentin-Plaster of Paris Combination with/without Platelet-Rich Plasma in the Treatment of Bone Defects Around Implants," *The International Journal of Oral & Maxillofacial Implants*, 2002; 17:86-94.

Klotzbuecher, C.M. et al. (Apr. 2000). "Patients with Prior Fractures Have an Increased Risk of Future Fractures: A Summary of the Literature and Statistical Synthesis," *J. Bone Miner. Res.* 15(4):721-739.
Kovacevic, D. et al. (Mar. 2008). "Biological Augmentation of Rotator Cuff Tendon Repair," *Clin. Orthop. Relat. Res.* 466(3):622-633.
Kovacs et al. "Comparative Study of b-Tricalcum Phosphate Mixed with Platelet-Rich Plasma versus β-Tricalcium Phosphate, A Bone Substitute Material in Dentistry," *Acts Veterinaria Hungarica*, 2003, 51(4):475-484.
Landesberg et al. "Quantification of Growth Factor Levels Using a Simplified Method of Platelet-Rich Plasma Gel Preparation," *J. Oral Maxillofac. Surg.*, 2000, 58:297-301.
Lasa et al. "Delivery of Demineralized Bone Powder by Fibrin Sealant," *Plast. Reconstr. Surg.*, 1995, 96(6):1409-1417.
Lasa Jr., C. et al. (1996). "Bone Induction by Demineralized Bone Powder and Partially Purified Osteogenin Using a Fibrin-Sealant Carrier," Chapter 14 in *Surgical Adhesives and Sealants: Current Technology and Applications*, Sierra, D. et al. eds., Technomic Publishing Company, Inc.: Lancaster, PA, pp. 135-144.
Lee, Y-M. et al. (Mar. 2000). "The Bone Regenerative Effect of Platelet-Derived Growth Factor-BB Delivered With a Chitosan/Tricalcium Phosphate Sponge Carrier," *J. Periodontal.* 71(3):418-424.
Lee, S.J. et al. (2001, e-pub. Feb. 13, 2001). "Molded Porous Poly ($_L$-Lactide) Membranes for Guided Bone Regeneration with Enhanced Effects by Controlled Growth Factor Release," *Journal of Biomedical Materials Research* 55:295-303.
Lee et al. "Enhanced bone formation by controlled growth factor delivery from chitosan-based biomaterials," *Journal of Controlled Release*, 2002, 78: 187-197.
Lekovic, V. et al. (Feb. 2002). "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," *J. Periodontol.* 73(2):198-205.
Letson, A.K. et al. (1994). "The Effect of Combinations of Growth Factors on Ligament Healing," *Clinical Orhopaedics and Related Research* 308:207-212.
Li, J. et al. (1994). "Systematic Administration of PDGF With or Without Alendronate Increases Spine and Whole Body Bone Mineral Density in OVX Rats," Abstract No. 59, *Sixteenth Annual Meeting of the American Society for Bone and Mineral Research*, Kansas City, MO., Sep. 9-13, 1994, p. S135.
Liang et al. (Sep. 2000). "Effect of Cytokines on Repair of Tendon Injury," *Pub Med* 14(5):283-285, Abstract Only.
Liang, H.W. et al. (Aug. 2009). "Effect of Platelet-Derived Growth Factor-BB on Proliferation of Tendon Cells Cultured in vitro," *Zhonghua Shao Shang Za Zhi*25(4):298-300, Abstract Only.
Lind et al. (1998). "Growth Factor Stimulation of Bone Healing," *Acta Orthopaedica Scandinavica Supplementum* Suppl. 283:2-37.
Lioubavina-Hack et al. "Methyl cellulose gel obstructed bone formation by GBR: an experimental study in rats," *J. Clin. Periodontol.*, 2005, 32:1247-1253.
Lioubavina-Hack et al. "Effect of Bio-Oss® with or without platelet-derived growth factor on bone formation by 'guided tissue regeneration': a pilot study in rats," *J Clin. Periodontol*, 2005, 32(12):1254-1260.
Lipshitz, H. et al. (Jun. 1975). "In Vitro Wear of Cartilage," *J. Bone Joint Surg. Am.* 57A(4):527-534.
Lynch, S.E. et al. (Nov. 1987). "Role of Platelet-Derived Growth Factor in Wound Healing: Synergistic Effects with Other Growth Factors," *Proc. Natl. Acad. Sci. USA* 84:76967700.
Lynch, S.E. et al. (1988). "Synergistic Effects of Recombinant Platelet-Derived Growth Factor Two and Insulin-Like Growth Factor-I in Wound Healing," Abstract No. 585, *J. Dental Res.* 67:186.
Lynch, S.E. et al. (1988). "Potential Role of Platelet-Derived and Insulin-Like Growth Factors in Periodontal Regeneration," Abstract No. 586, *J. Dental Res.* 67:186.
Lynch, S.E. et al. (Dec. 1988). "Growth Factors in Wound Healing: Single and Synergistic Effects," Abstract No. 238, *J. Cell Biol.* 107(6 Part 3):46a.

Lynch, S.E. et al. (1989). "Comparative Effects of Growth Factors on Soft Tissue Repair," Abstract No. 1153, *J. Dental Res.* 68:326.

Lynch, S.E. et al. (1989). "A Combination of Platelet-Derived and Insulin-Like Growth Factors Enhances Periodontal Regeneration," *J. Clin. Periodontol.* 16:545-548.

Lynch, S.E. (1990). "A Possible Role for Polypeptide Growth and Differentiation Factors in Periodontal Regeneration," *Executive Committee on Chemotherpeutics; Amer. Acad Peridontal-Position Paper* pp. 1-4.

Lynch, S.E. et al. (Jul. 1991). "The Effects of Short Term Application of a Combination of Platelet-Derived and Insulin-Like Growth Factors on Periodontal Wound Healing," *J. Periodontol.* 62(7):458-467.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," *J. Periodontol.* 62(11):710-717.

Lynch, S.E. (1991). "Platelet-Derived Growth Factor and Insulin-Like Growth Factor. I: Mediators of Healing Soft Tissue and Bone Wounds," *Periodontol Case Reports NE Soc. Periodontists Bull.* 13(2):13-20.

Lynch, S.E. et al. (1992). "Effect of PDGF-B and IGF-I on Bone Regeneration," Abstract No. 82, *J. Dental Res.* 71:116.

Lynch, S.E. (1993). "Comparison of Results in the Canine and Primate Models Using a Single Regenerative Therapy," Abstract No. 37, *J. Dental Res.* 72:108.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," *Wound Rep. Reg.* 2(3):182-190.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," *Wound Repair and Regeneration* Abstract, 2(1):84.

Lynch, S.E. et al. (1994). "Polypeptide Growth Factors: Molecular Mediators of Tissue Repair," Chapter 33 in *Molecular Pathogenesis of Periodontal Disease*, Genco, R. et al eds., A.S.M. Press: Washington DC, pp. 415-425.

Lynch, S.E. (1994). "The Role of Growth Factors in Periodontal Repair and Regeneration," Chapter 11 in *Periodontal Regeneration: Current Status and Directions*, Polson, A. ed. Quintessence Publishing Co, Inc: Chicago, IL, 11:179-197.

Lynch, S.E. (1995). "Introduction," in *Tissue Engineering: Applications in Maxillofacial Surgery and Preiodontics*, Lynch, S.E. et al. eds., Quintessence Publishing, pp. xi-xvi.

Lynch, S.E. (2005). "Bone Regeneration Techniques in the Orofacial Region," Chapter 18 in *Bone Regeneration and Repair: Biology and Clinical Applications*, Lieberman, J.R. et al. eds., Humana Press Inc.: Totowa, NJ, pp. 359-390.

Lynch, S.E. et al. (Dec. 2006). "A New Era in Periodontal and Periimplant Regeneration: *Use of Growth-Factor Enhanced Matrices Incorporating rhPDGF*," *Compendium of Continuing Education in Dentistry* 27(12):672-679.

Lynch, S.E. et al. (2008). "Use of rhPDGF to Improve Bone and Periodontal Regeneration," Chapter 6 in *Tissue Engineering: Applications in Maxillofacial Surgery and Periodontics*, Second Edition, Lynch, S.E. et al. eds., Quintessence Publishing Co.: Hanover Park, IL, pp. 87-102.

Maiorana et al. "Maxillary Sinus Augmentation with Anorganic Bovine Bone (Bio-Oss) and Autologous Platelet-Rich Plasma: Preliminary Clinical and Histologic Evaluations," *Int J Periodontics Restorative Den*, 2003, 23(3):227-235.

Manske et al. (Feb. 1985). "Flexor Tendon Healing," *Symposium on Flexor Tendon Surgery, Hand Clinics* 1(1):25-34.

Marcopoulou et al. (2003). "Proliferative Effect of Growth Factors TGF-β1, PDGF-BB, and rhBMP-2 on Human Gingival Fibroblasts and Periodontal Ligament Cells," *Journal of International Academy of Periodontology* 5(3):63-70.

Marx, R.E. et al. (2005). "Bisphosphonate-Induced Exposed Bone (Osteonecrosis/Osteoperosis) of the Jaws: Risk Factors, Recognition, Prevention, and Treatment," *J. Oral Maxillofac. Surg.* 63:1567-1575.

Marx, R.E. (2008). "Application of Tissue Engineering Principles to Clinical Practice," Chapter 4 in *Tissue Engineering: Applications in Maxillofacial Surgery and Periodontics*, Second Edition, Lynch, S.E. et al. eds., Quintessence Publishing Co.: Hanover Park, IL, pp. 47-63.

Marx, R.E. (2008). "Use of PRP in Oral and Maxillofacial Surgery and Periodontology," Chapter 9 in *Tissue Engineering: Applications in Maxillofacial Surgery and Periodontics*, Second Edition, Lynch, S.E. et al. eds., Quintessence Publishing Co.: Hanover Park, IL, pp. 132-144.

Mayfield, L. et al. (Oct. 1998). "Clinical and Radiographic Evaluation, Following Delivery of Fixed Reconstructions, at GBR Treated Titanium Fixtures," *Clin. Oral Implants Res.* 9:292-302.

McAllister, B. et al. (1998). "Long-term Evaluation of Sinus Grafting with Bio-Oss® in the Chimpanzee," Abstract No. 1097, *J. Dental Res.* 77:769.

McAllister et al. "Eighteen-month Radiographic and Histologic Evaluation of Sinus Grafting with A-rganic Bovine Bone in the Chimpanzee," *The International Journal of Oral & Maxillofacial Implants*, 1999, 14(3):361-368.

McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," *J. Orthop. Res.* 27(8):1033-1042, Abstract Only.

McGuire, M.K. et al. (2006). "rhPDGF-BB Promotes Healing of Periodontal Defects: 24-Month Clinical and Radiographic Observations," *Int. J. Periodontics Restorative Dent.* 26(3):223-231.

McGuire, M.K. (2008). "Soft Tissue Engineering Applications in Dentistry," Chapter 7 in *Tissue Engineering: Applications in Maxillofacial Surgery and Periodontics*, Second Edition, Lynch, S.E. et al. eds., Quintessence Publishing Co.: Hanover Park, IL, pp. 103-118.

McMurty, R.Y. et al. (1992). "Fractures of the Distal Radius," Chapter 35 in *Skeletal Trauma*, Browner B.D. et al. eds., W.B. Saunders Company: Philadelphia, PA, 2:1063-1094.

Mehta, V. et al. (Apr.-Jun. 2005). "The Use of Growth Factors on Tendon Injuries," *Journal of Hand Therapy* 18:87-92.

Melo, M.D. et al. (Dec. 2005). "Osteonecrosis of the Jaws in Patients with a History of Receiving Bisphosphonate Therapy. Strategies for Prevention and Early Recognition," *J. American Dental Association* 136:16751681.

Migliorati, C.A. et al. (Jun. 2006). "Bisphosphate-Associated Osteonecrosis: A Long Term Complication of Bisphophonate Treatment," *Lancet Oncol.* 7:508-514.

Mitlak et al. "The Effect of Systemically Administered PDGF-BB on the Rodent Skeleton," *Journal of Bone and Mineral Research*, 1996, 11(2):238-247.

Molloy, T. et al. (2003). "The Roles of Growth Factors in Tendon and Ligament Healing," *Sports Med.* 33(5):381-394.

Mont, M.A. et al. (Oct. 1998). "Osteonecrosis of the Femoral Head. Potential Treatment with Growth and Differentiation Factors," *Clin. Orthop. Relat. Res.* 355(Suppl.):S314-S335, Abstract Only, 2 pages.

Morris, G.J. et al. (Jan. 2007). "Bisphosphonate Therapy for Women with Breast Cancer and at High Risk for Osteoporosis," *Journal of the National Medical Association* 99(1):35-45.

Mott, D.A. et al. (2002). "Enhancement of Osteoblast Proliferation in vitro by Selective Enrichment of Demineralized Freeze-Dried Bone Allograft with Specific Growth Factors," *J. Oral Implantol.* 28(2):57-66.

Mumford, J.H. et al. (Mar. 2001). "The Effects of Platelet Derived Growth Factor-BB on Periodontal Cells in In Vitro Wound Model," *J. Periodontal.* 72(3):331-340.

Nakamura, N. et al. (1998). "Early Biological Effect of in Vivo Gene Transfer of Platelet-derived Grown Factor (PDGF)-B into Healing Patellar Ligament," *Gene Therapy* 5:1185-1170.

Nancollas, G.H. et al. (2006, e-pub. Jul. 2005). "Novel Insights into Actions of Bisphosphonates on Bone: Differences in Interactions with Hydrozyapatite," *Bone* 38:617-627.

Nase, J.B. et al. (Aug. 2006). "Osteonecrosis of the Jaw and Oral Bisphosphonate Treatment," *J. American Dental Association* 137:1115-1119.

Nash, T.J. et al. (Mar. 1994). "Effect of Platelet-Derived Growth Factor on Tibial Osteotomies in Rabbits," *Bone* 15(2):203-208.

Nevins, M.L. et al. (2003). "Evaluation of Periodontal Regeneration Following Grafting Intrabony Defects with Bio-Oss® Collagen: A Human Histologic Report," *Int. J. Periodont. Rest. Dent.* 23(1):9-17.

Nevins et al. "Periodontal Regeneration in Humans Using Recombinant Human Platelet-derived Growth Factor-BB (rhPDGF-BB) and Allogenic Bone," J. Periodontal, Sep. 2003, 74(9):1282-1292.

Nevins, M.L. et al. (2005). "Three-Dimensional Micro-Computed Tomographic Evaluation of Periodontal Regeneration: A Human Report of Intrabony Defects Treated with Bio-Oss Collagen," Int. J. Periodontics Restorative Dent. 25(4):365-373.

Nevins et al. "Platelet-Derived Growth Factor Stimulates Bone Fill and Rate of Attachment Level Gain: Results of a Large Multicenter Randomized Controlled Trial," J. Periodontal, 2005, 76(12) :2205-2215.

Nevins, M. et al. (Oct. 2007). "Clinical Results Using Recombinant Human Platelet-Derived Growth Factor and Mineralized Freeze-Dried Bone Allograft in Periodontal Defects," Int. J. Periodontics Restorative Dent. 27(5):421-427.

Nevins, M. et al. (2008). "Treatment of Advanced Periodontal Defects Using Bioactive Therapies," Chapter 5 in Tissue Engineering: Applications in Maxillofacial Surgery and Periodontics, Second Edition, Lynch, S.E. et al. eds., Quintessence Publishing Co.: Hanover Park, IL, pp. 67-86.

Nevins, M.L. et al. (2008). "Site Development for Implant Placement: Regenerative and Esthetic Techniques in Oral Plastic Surgery," Chapter 8 in Tissue Engineering: Applications in Maxillofacial Surgery and Periodontics, Second Editions, Lynch, S.E. et al. eds., Quintessence Publishing Co.: Hanover Park, IL, pp. 119-131.

Nickols, J.C. et al. (2008). "The Role of Growth Factors in Tendon Healing," Chapter 20 in Tissue Engineering: Applications in Maxillofacial Surgery and Periodontics, Second Edition, Lynch, S.E. et al. eds., Quintessence Publishing Co.: Hanover Park, IL, pp. 276-289.

Nociti, F.H. Jr. et al. (2000). "Histometric Evaluation of Bone Regeneration Around Immediate Implants Partially in Contact with Bone: A Pilot Study in Dogs," Implant Dentistry 9(4):321-328.

Non-Final Office Action mailed on Jul. 27, 2007, for U.S. Appl. No. 11/159,533, filed Jun. 23, 2005, 13 pages.

Non-Final Office Action mailed on Oct. 31, 2008, for U.S. Appl. No. 11/159,533, filed Jun. 23, 2005, 11 pages.

Non-Final Office Action mailed on Oct. 16, 2009, for U.S. Appl. No. 11/704,685, filed Feb. 9, 2007, 19 pages.

Non-Final Office Action mailed on Jul. 7, 2010, for U.S. Appl. No. 12/323,183, filed Nov. 25, 2008, 11 pages.

Non-Final Office Action mailed on Sep. 14, 2010, for U.S. Appl. No. 11/601,376, filed Nov. 17, 2006, 18 pages.

Non-Final Office Action mailed on Sep. 23, 2010, for U.S. Appl. No. 12/513,491, filed Nov. 5, 2007, 10 pages.

Notice of Allowance mailed on Apr. 23, 2010, for U.S. Appl. No. 11/704,685, filed Feb. 9, 2007, 10 pages.

Oberg, S. et al. (Apr. 1994). "Bone Healing After Implantation of Hydroxyapatite Granules and Blocks (Interpore 200) Combined with Autolyzed Antigen-Extracted Allogeneic Bone and Fibrin Glue. Experimental Studies on Adult Rabbits," International Journal of Oral and Maxillofacial Surgery 23(2):110-114, abstract only.

Orbay, J.L. et al. (Jan. 2004). "Volar Fixed-Angle Plate Fixation for Unstable Distal Radius Fractures in the Elderly Patient," J. Hand Surg. 29A(1):96-102.

Orthovita, Inc. (Dec. 14, 2000). "510(k) Summary. Vitoss™ Scaffold Syntehtic Cancellous Bone Void Filler," located at <http://www.accessdata.fda.gov/cdrh_docs/pdf/k994337.pdf>, last visited on Mar. 30, 2010, 6 pages.

Orthovita, Inc. (Nov. 19, 2002). "Morningstar® Document Research™. Form 10-Q, Quarterly Repot Which Provides a Continuing View of a Company's Financial Position," located at <http://orthovita.com/investors/secfilings.aspx>, last visited on Jun. 17, 2010, 48 pages.

Orthovita, Inc. (2009). "Architects of the New Biomaterials Age, 2008 Annual Report," located at <http://orthovita.com/investors/annual-reports/previousreports.aspx>, last visited on Jun. 17, 2010, 93 pages.

Owen et al. (1984). "Simian Sarcoma Virus-Transformed Cells Secrete a Mitogen Identical to Platelet-Derived Growth factor," Science 25:54-56.

Palti, A. et al. (2002). "A Concept for the Treatment of Various Dental Bone Defects," Implant Dentistry 11(1):73-78.

Parashis, A. et al. (Jul. 1998). "Comparison of 2 Regenerative Procedures—Guided Tissue Regeneration and Demineralized Freeze—Dried Bone Allograft—in the Treatment of Intrabony Defects: A Clinical and Radiographic Study," J. Periodontol. 69(7):751-758.

Park et al. (1995). "Periodontal Regeneration in Class III Furcation Defects of Beagle Dogs Using Guided Tissue Regenerative Therapy with Platelet-Derived Growth Factor," J. Periodontol. 66:462-477.

Paul, W. et al. (1999). "Development of Porous Spherical Hydroxyapatite Granules: Application Towards Protein Delivery," J. Mater. Sci. Mater. Med. 10:383-388.

Persson, G.R. et al. (2000). "A Retrospective Radiographic Outcome Assessment Study of Intra-Bony Defects Treated by Osseous Surgery or by Bone Graft Procedures," J. Clin. Periodontol. 27:104-108.

Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts,"Arch. Orthop. Trauma Surg. 123(9):485-488.

Pfeilschifter, J. et al. (Jul.-Dec. 1990). "Stimulation of Bone Matrix Apposition in Vitro by Local Growth Factors: A Comparison Between Insulin-Like Growth Factor I, Platelet Derived Growth Factor, and Transforming Growth Factor," Endocrinology 127(1):69-75.

Philippart et al. "Human Recombinant Tissue Factor, Platelet-rich Plasma, and Tetracycline Induce a High-Quality Human Bone Graft A 5-year Survey," The International Journal of Oral and Maxillofacial Implants, 2003, 18(3):411-416.

Phillips, S. et al. (1988). "The Direct Medical Costs of Osteoporosis for American Woman Aged 45 and Older, 1986," Bone 9(4):271-279.

Pickett, F.A. (Jul. 2006). "Bisphosphonate-Associated Osteonecrosis of the Jaw: A Literature Review and Clinical Practice Guidelines," Journal of Dental Hygiene 80(3):1-12.

Pietrzak, W.S. et al. (Jul. 2000). "Calcium Sulfate Bone Void Filler: A Review and a Look Ahead," J. Craniofac. Surg. 11(4):327-333; discussion p. 334.

Polverini, P.J. (Aug. 2002). "Angiogenesis in Health and Disease: Insights into Basic Mechanisms and Therapeutic Opportunities," Journal of Dental Education 66(8):962-975.

Qiu, Y. et al. (2009). "Combination of PDGF-BB and bFGF Reduces Differentiation but Maintains Proliferation of Human Tenocytes in Low Bovine Serum Culture in vitro," European Cells and Materials 18(Suppl. 2):86.

Qu, Z. et al. (Nov. 1994). "Immunolocalization of Basic Fibroblast Growth Factor and Platelet-Derived Growth Factor-A During Adjuvant Arthritis in the Lewis Rat," Am. J. Pathol. 145(5):1127-1139.

R&D Systems, Inc. (Date Unknown). "Quantikine® Human PDGF-BB Immunoassay," Package Insert, Catalog No. DBB00, SBB, and PDB00, located at <http://www.rndsystems.com/pdf/dbb00.pdf>, last visited on Mar. 30, 2010, 16 pages.

Rao, C.D. et al. (Apr. 1986). "Structure and Sequence of the Human C-Sis Platelet-Derived Growth Factor 2 (SIS/PDGF2) Transcriptional Unit," Proc. Natl. Acad. Sci. USA 83:2392-2396.

Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," Int. J. Mol. Med. 23(3):407-413, Abstract Only, 2 pages.

Rasubala, L. et al. "Platelet-derived Growth Factor and Bone Morphogenetic Protein in the Healing of Mandibular Fractures in Rats," British Journal of Oral and Maxillofacial Surgery, 2003, 41:173-178.

Response to Advisory Action submitted on Apr. 28, 2008, for U.S. Appl. No. 11/159,533, filed Jun. 23, 2005, 15 pages.

Response to Notice of Non-Compliant Amendment submitted on Nov. 2, 2007, for U.S. Appl. No. 11/159,533, filed Jun. 23, 2005, 7 pages.

Riley, G. (2004, e-pub. Jul. 16, 2003). "The Pathogenesis of Tendinopathy. A Molecular Perspective," Rheumatology 43(2):131-142.

Robbins, K.C. et al. (Oct. 13, 1983). "Structural and Immunological Similarities Between Simian Sarcoma Virus Gene Product(s) and Human Platelet-Derived Growth Factor," Nature 305:605-608.

Rodeo, S.A. et al. (Dec. 1993). "Tendon Healing in a Bone Tunnel," J. Bone Joint Surg. Am. 75-A(12):1795-1803.

Rodeo, S.A. et al. (1999). "Use of Recombinant Human Bone Morphogenic Protein-2 to Enhance Tendon Healing in a Bone Tunnel," *Am. J. Sports Med.* 27(4):476-488.

Rodriguez et al. "Maxillary Sinus Augmentation with Deproteinated Bovine Bone and Platelet Rich Plasma with Simultaneous Insertion of Endosseous Implants," *J. Oral Maxiilofac. Surg.*, 2003, 61 :157-163.

Rohrich et al. (Nov. 1999). "Mersilene Suture as a Vehicle for Delivery of Growth Factors in Tendon Repair," *Journal of the American Society of Plastic Surgeons* 104(6):1713-1717.

Rolf, C.G. et al. (2001). "Increased Cell Proliferation and Associated Expression of PDGFRβ Causing Hypercellularity in Patellar Tendinosis," *Rheumatology* 40:256-261.

Ruggiero, S.L. et al. (2006, e-pub. Jul. 31, 2006). "Bisphosphonate-Related Osteoncerosis of the Jaw: Background and Guidelines for Diagnosis, Staging and Management," *Oral Surgery, Oral Medicine, Oral Pathology, Oral Radiology, and Endodontology* <http://www.sciencedirect.com/science/journal/10792104>, 8 pages.

Ruiz, G. et al. (1991). "Short Term Administration of Growth Factors Enhances Periodontal Regeneration," Abstract No. 1615, *J. Dental Res.* 70:468.

Russell, T.A. et al. (Date Unknown). "Trigen® IM Nail System Surgical Technique. Trochanteric Antegrade Nail (TAN™)," 24 pages.

Rutherford et al. (1992). "Platelet-Derived and Insulin-Like Growth Factors Stimulate Regeneration of Periodontal Attachment in Monkeys," *Journal of Periodontal Research* 27(4-Part 1):285-290.

Sakiyama-Elbert, S.E. et al. (Nov. 2008). "Controlled-Release Kinetics and Biologic Activity of Platelet-Derived Growth Factor-BB for Use in Flexor Tendon Repair," *J. Hand Surg. Am.* 33(9):1548-1557, Abstract Only.

Sandberg, "Matrix in Cartilage and Bone Development: Current Views on the Function and Regulation of Major Organic Components," *Annals of Medicine*, 1991, 23:207-217.

Sarment, D.P. et al. (Feb. 1, 2006). "Effect of rhPDGF-BB on Bone Turnover During Periodontal Repair," *Journal of Clinical Periodontolgy* 33(2):135-140.

Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," *Clin. Oral Implants Res.* 14(3):369-372.

Sasai, Y. et al. (1994). "Xenopus *chordin*: A Novel Dorsalizing Factor Activated by Organizer-Specific Homeobox Genes," *Cell* 79:779-790.

Saygin et al. "Molecular and Cell Biology of Cementum," *Periodontology*, 2000, 24:73-98.

Schenk, R.K. et al. (Jan./Feb. 1994). "Healing Pattern of Bone Regeneration in Membrane-Protected Defects: A Histologic Study in the Canine Mandible," *Int. J. Oral Maxillofac. Implants* 9(1):13-29.

Schmidt, C.C. et al. (Mar. 1995). "Effect of Growth Factors on the Proliferation of Fibroblasts from the Medial Collateral and Anterior Cruciate Ligaments," *J. Orthop. Res.* 13(2):184-190, Abstract Only.

Schmidt et al. "A review of the effects of insulin-like growth factor and platelet derived growth factor on in vivo cartilage healing and repair," *Osteoarthritis and Cartilage*, 2006, 14(5):403412.

Schmidt, M.B. et al. (2008). "Tissue Engineering Strategies in the Treatment of TMDs," Chapter 18 in *Tissue Engineering: Applications in Maxillofacial Surgery and Periodontics*, Second Edition, Lynch, S.E. et al. eds., Quintessence Publishing Co.: Hanover Park, IL, pp. 252-264.

Schmitt, J.M. et al. (Nov. 1997). "Comparison of Porous Bone Mineral and Biologically Active Glass in Critical-Sized Defects," *J. Periodontol.* 68(11):1043-1053.

Schnabel, L.V. et al. (Feb. 2007). "Platelet Rich Plasma (PRP) Enhances Anabolic Gene Expression Patterns in Flexor Digitorum Superficialis Tendons," *J. Orthop. Res.* 25(2):230-240, Abstract Only.

Secinfo.com (Mar. 31, 2003). "Interpore International Inc/DE 10-K for Dec. 31, 2002," located at <http://www.secinfo.com/dV179.2kp.htm, last visited on May 20, 2010, 57 pages.

Shahgaldi, B.F. et al. (Jan. 1991). "Repair of Cartilage Lesions Using Biological Implants. A Comparative Histological and Biomechanical Study in Goats," *J. Bone Joint Surg. Br.* 73-B(1):57-64.

Sharma, P. et al. (2008). "Tendinopathy and Tendon Injury: The Future," *Disability and Rehabilitation* 30(20-22):1733-1745.

Sigma (Date Unknown). "Platelet Derived Growth Factor-BB," Product Information Sheet, 2 pages.

Simion, M. et al. (Apr. 1994). "A Comparative Study of the Effectiveness of e-PTFE Membranes With and Without Early Exposure During the Healing Period," *Int. J. Periodontics Restorative Dent.* 14(2):166-180.

Simion, M. et al. (1994). "Vertical Ridge Augmentation Using a Membrane Technique Associated with Osseointegrated Implants," *Int. J. Periodontics Restorative Dent.* 14(6):497511.

Simion, M. et al. (1995). "Bacterial Penetration in vitro Through GTAM Membrane With and Without Topical Chlorhexidine Application: A Light and Scanning Electron Microscopic Study," *J. Clin. Periodontol.* 22:321-331.

Simion, M. et al. (Feb. 1998). "Vertical Ridge Augmentation Around Dental Implants Using a Membrane Technique and Autogenous Bone or Allografts in Humans," *Int. J. Periodontics Restorative Dent.* 18(1):9-23.

Simion, M. et al. (1999). "Effect of Different Microstructures of e-PTFE Membranes on Bone Regeneration and Soft Tissue Response: A Histologic Study in Canine Mandible," *Clin. Oral Implants Res.* 10:73-84.

Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," *The International Journal of Periodontics & Restorative Dentistry* 26(5):415-423.

Simion, M. et al. (2008). "Minimally Invasive Strategies for Vertical Ridge Augmentation," Chapter 10 in *Tissue Engineering: Applications in Maxillofacial Surgery and Periodontics*, Second Edition, Lynch, S.E. et al. eds., Quintessence Publishing Co.: Hanover Park, IL, pp. 145-158.

Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," *Mayo Clin. Proc.* 81(8):1013-1022.

Smith & Nephew (Date Unknown). "Trigen. Humeral Nail," Surgical Technique Pamphlet, 27 pages.

Solheim, E. "Growth Factors in Bone," *International Orthopedics (SICOT)*, 1998, 22:410-416.

Spector, M. (2008). "Basic Principles of Scaffolds in Tissue Engineering," Chapter 2 in *Tissue Engineering: Applications in Maxillofacial Surgery and Periodontics*, Second Edition, Lynch, S.E. et al., Quintessence Publishing Co.: Hanover Park, IL, pp. 26-36.

Spindler, K.P. et al. (1995). "Proliferative Response to Platelet-Derived Growth Factor in Young and Old Rat Patellar Tendon," *Connective Tissue Research* 31(2):171-177.

Spindler, K.P. et al. (Jul. 1996). "Patellar Tendon and Anterior Cruciate Ligament Have Different Mitogenic Responses to Platelet-Derived Growth Factor and Transforming Growth Factor β," *Journal of Orthopaedic Research* 14(4):542-546.

Stephan, E.B. et al. (Apr. 1999). "Anogranic Bovine Bone Supports Osteoblastic Cell Attachment and Proliferation," *J. Periodontol.* 70(4):364-369.

Stephan et al. "Platelet-Derived Growth Factor Enhancement of a Mineral-Collagen Bone Substitute," *J. Periodontal*, Dec. 2000, 71:1887-1892.

Strom, T.B. (Sep. 6, 2005). "Saving Islets from Allograft Rejection," *PNAS USA* 102(36):12651-12652.

Suba et al. "Facilitation of β-Tricalcium Phosphate-Induced Alveolar Bone Regeneration by Platelet-Rich Plasma in Beagle Dogs: A Histologic and Histomorphometric Study," *The International J. of Oral and Maxillofacial Implants*, 2004, 19(6):832-838.

Supplemental Response to Advisory Action of Jun. 4, 2008, submitted on Jun. 9, 2008, for U.S. Appl. No. 11/159,533, filed on Jun. 23, 2005, 15 pages.

Supplementary European Search Report mailed on Aug. 29, 2008, for EP Application No. 05803356.4, filed on Oct. 12, 2005, 7 pages.

Tadic, D. et al. (2004). "A Novel Method to Produce Hydroxyapatite Objects with Interconnecting Porosity that Avoids Sintering," *Biomaterials* 25(16):3335-3340.

Tamai, N. et al. (2002). "Novel Hydroxyapatite Ceramics with an Interconnective Porous Structure Exhibit Superior Osteoconduction in vivo," *J. Biomed. Mater. Res.* 59:110-117.

Teraoka, K. et al. (2004). "Construction of an Interconnected Pore Network Using Hydroxyapatite Beads," *Key. Eng. Mater.* 254-256:257-259.

Teraoka, K. et al. (Sep. 2004). "Construction of Interconnected Pore Network Using Hydroxyapatite Small Components," *Trans. Mater. Res. Soc. Jpn.* 29(6):2919-2921.

Thompoulos, S. et al. (May 2005). "Effect of Several Growth Factors on Canine Flexor Tendon Fibroblast Proliferation and Collagen Synthesis in vitro," *J. Hand Surg. Am.* 30(3):441-447, Abstract Only.

Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," *J. Orthop. Res.* 25(17):1358-1368.

Thomopoulos, S. et al. (Sep. 2009, e-pub. Mar. 25, 2009). "Enhanced Flexor Tendon Healing through Controlled Delivery of PDGF-BB," *J. Orthop. Res.* 27(9):1209-1215, Abstract Only.

Thomopoulos, S. et al. (Feb. 2010, e-pub. Nov. 24, 2009). "bFGF and PDGF-BB for Tendon Repair: Controlled Release and Biologic Activity by Tendon Fibroblasts in Vitro," *Ann. Biomed. Eng.* 38(2):225-234.

Tinti, C. et al. (1996). "Vertical Ridge Augmentation: What is the Limit?" *Int. J. Periodontics Restorative Dent.* 16(3):221-229.

TRENDING123.Com (Date Unknown). "Stock Sectors. Medical Instruments SupIs," located at <http://www.trending123.com/stock-sectors/Medical_Instruments_Supls.html>, last visited on May 3, 2010, 11 pages.

U.S. Appl. No. 10/965,319, filed Oct. 14, 2004, by Lynch.

Van Den Wyngaert, T. et al. (Aug. 2006). "Bisphosphonates and Osteonecrosis of the Jaw: Cause and Effect or a *post hoc* Fallacy?" *Annals of Oncology* 17(8):1197-1204.

Venkatasatya, M. et al. (2008). *The Effect of PDGF, Vitamin D and PTH on Osteoblasts Derived From Patients on Chronic Bisphosphonate Therapy*, Dissertation for The State University of New York at Buffalo, located at <http://gradworks.umi.com/14/531/1453440.html>, last visited on Mar. 31, 2010, 2 pages, Abstract Only.

Virchenko, O. et al. (2008, e-pub. Jul. 4, 2008). "Early Achilles Tendon Healing in Sheep," *Arch. Orthop. Trauma Surg.* 128:1001-1006.

Visnapuu et al. "Distribution of fibroblast growth factors (FGFR-1 and -3) and platelet-derived growth factor receptors (PDGFR) in the rat mandibular condyle during growth," *Orthod. Craniofadal.* 2002, 5:147-153.

Walter, C. et al. (2006, e-pub. Aug. 29, 2006). "Prevalence of Bisphophonate Associated Osteonecrosis of the Jaw within the Filed of Osteonecrosis," *Support Care Center* 6 pages.

Wang, Y. et al. (Feb. 23, 1996). "A Large Family of Putative Transmembrane Receptors Homologous to the Product of the Drosophila Tissue Polarity Gene Frizzled," *J. Biol. Chem.* 271(8):4468-4476.

Wang, L. et al. (2004). "Three-Dimensional Porous Network Structure Developed in Hydroxyapatite-Based Nanocomposites Containing Enzyme Pretreated Silk Fibronin," *J. Nanopart.* 6(1):91-98.

Wang, X.T. et al. (Sep. 2004). "Tendon Healing in Vitro: Genetic Modification of Tenocytes With Exogenous PDGF Gene and Promotion of Collagen Gene Expression," *The Journal of Hand Surgery* 29A(5):884-890.

Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," *J. Bone Joint Surg. Am.* 74-A(1):36-45.

Wei et al. "Nano-Fibrous Scaffold for Controlled Delivery of Recombinant Human PDGF-BB," *Journal of Controlled Release*, 2006, e-pub. Mar. 3, 2006, 112:103-110.

White, E. et al. (1986). "Biomaterial Aspects of Interpore-200 Porous Hydroxyapatite," *Dent. Clin. North Am.* 30(1):49-67, Abstract only.

Wiesen, R.J. et al. (1998). "Efficacy of Bovine Bone Mineral in Vertical Osseous Defects," Abstract No. 1165, *J. Dental Res.* 77:777.

Wikesjö et al. (1988). "Repair of Periodontal Furcation Defects in Beagle Dogs Following Reconstructive Surgery Including Root Surface Demineralization with Tetracycline Hydrochloride and Topical Fibronectin Application," *J. Clin. Periodontol* 15:73-79.

Wikesjö et al. (1989). "Effects of Subgingival Irrigation on A. actinomycetemcomitans," *J. Clin. Perrodont.* 16:116-119.

Williams et al. "Tissue Engineering: What Does It Mean? Why Is It Important?" *Compendium*, Jan. 2005, 26(1):54-60.

Wisner-Lynch, L.A. (Oct. 2006). "From Passive to Active: Will Recombinant Growth Factor Therapeutics Revolutionize Regeneration?" *Int. J. Periodont. And Rest. Dent.* 26(5):409-41 1.

Wong, M.W. et al. (Oct. 2003). "Effect of Dexamethasone on Cultured Human Tenocytes and its Reversibility by Platelet-Derived Growth Factor," *Journal of Bone and Joint Surgery American* 85-A(10)1914-1920, Abstract Only.

Woo, S.L-Y. et al. (1998). "Engineering the Healing of the Rabbit Medical Collateral Ligament," *Medical and Biological Engineering and Computing* 36:359-364.

Woo, S-B. et al. (May 16, 2006). "Systematic Review: Bisphosphonates and Osteonecrosis of the Jaws," *Annals of Internal Medicine* 144(10):753-761.

Written Opinion of the International Searching Authority mailed on Aug. 3, 2007, for PCT Application No. PCT/US07/003582, filed on Feb. 8, 2007, 7 pages.

Written Opinion of the International Searching Authority mailed on Oct. 2, 2007, for PCT Application No. PCT/US05/36447, filed on Oct. 12, 2005, 4 pages.

Written Opinion of the International Searching Authority mailed on Dec. 7, 2007, for PCT Application No. PCT/US2006/044766 filed on Nov. 17, 2006, 6 pages.

Written Opinion of the International Searching Authority mailed on Aug. 4, 2008, for PCT Patent Application No. PCT/US2008/065666, filed on Jun. 3, 2008, 7 pages.

Written Opinion of the International Searching Authority mailed on May 20, 2009, for PCT Application No. PCT/US2007/083638, filed on Nov. 5, 2007, 6 pages.

Written Opinion of the International Searching Authority mailed on Jul. 8, 2009, for PCT Application No. PCT/US2008/054354, filed on Feb. 20, 2008, 10 pages.

Written Opinion of the International Searching Authority mailed on Jun. 26, 2009, for PCT Application No. PCT/US2009/033596, filed on Feb. 9, 2009, 6 pages.

Yang, C. et al. (2003). "Vascular Endothelial Growth Factor Gene Transfection to Enhance the Repair of Avascular Necrosis of the Femoral Head of Rabbit," *Chinese Medical Journal* 116(10):1544-1548.

Yazawa et al. "Basic Studies on the Clinical Applications of Platelet-Rich Plasma," *Cell Transplantation*, 2003, 12:509-518.

Yazawa, M. et al. (May 2004). "Basic Studies on the Bone Formation Ability by Platelet Rich Plasma in Rabbits," *Journal of Craniofacial Surgery* 15(3):439-446.

Yokota, K. et al. (2008, e-pub. Feb. 1, 2008). "Platelet-Rich Plasma Accelerated Surgical Angio-Genesis in Vascular Necrotic Bone. An Experimental Study in Rabbits," *Acta Orhopaedica* 79(1):106-110.

Younger, E.M. et al. (1989). "Morbidity at Bone Graft Donor Sites," *J. Orthop. Trauma* 3(3):192-195.

Zavras, a.I. et al. (2006). "Bisphosphonates Are Associated With Increased Risk for Jaw Surgery in Medical Claims Data: Is it Osteonecrosis?" *J. Oral Maxillofac. Surg.* 64:917-923.

Zhu et al. "Gene Transfer and Expression of Platelet-Derived Growth Factors Modulate Periodontal Cellular Activity," *J. Dent Res*, 2001, 80(3):892-897.

Zimmer, Inc. (2005). "Zimmer® Collagen Repair Patch," Product No. 04-4100-001-00, 6 pages.

Amendment in Response to Non-Final Office Action submitted on Oct. 6, 2010, for U.S. Appl. No. 12/323,183, filed Nov. 25, 2008, 11 pages.

Final Office Action mailed on Jan. 7, 2011, for U.S. Appl. No. 12/323,183, filed Nov. 25, 2008, 9 pages.

International Search Report mailed on Apr. 27, 2010, for PCT Patent Application No. PCT/US2010/026450, filed on Mar. 5, 2010, 1 page.

Non-Final Office Action mailed on Oct. 21, 2010, for U.S. Appl. No. 11/778,498, filed Jul. 16, 2007, 18 pages.

Premdas, J. et al. (2001). "The Presence of Smooth Muscle Action in Fibroblasts in the Torn Human Rotator Cuff," *Journal of Orthopaedic Research* 19:221-228.

Written Opinion of the International Searching Authority mailed on Apr. 27, 2010, for PCT Patent Application No. PCT/US2010/026450, filed on Mar. 5, 2010, 6 pages.

Amendment in Response to Non-Final Office Action submitted on Jan. 14, 2011, for U.S. Appl. No. 11/601,376, filed Nov. 17, 2006, 14 pages.

* cited by examiner

METHODS FOR TREATMENT OF DISTRACTION OSTEOGENESIS USING PDGF

CROSS REFERENCE TO RELATED APPLICATIONS

This application claims the benefit under 35 U.S.C. §119 (e) of U.S. Provisional Application Ser. No. 61/026,934, filed Feb. 7, 2008, the contents of which are incorporated herein by reference in their entirety.

FIELD OF THE INVENTION

The present invention relates to compositions and methods for use in osteodistraction procedures.

BACKGROUND OF THE INVENTION

Osteodistraction or distraction osteogenesis is the process by which the slow, incremental distraction of fracture callus is used to stimulate and prolong active bone formation, thereby providing a means of bridging what would otherwise be a large bony defect. Distraction osteogenesis is used in the reconstruction of skeletal deformities and the lengthening of bones, such as in the treatment of pediatric limb length inequality.

In osteodistraction procedures, the bone is surgically split in two segments, and the two ends of the bone are gradually moved apart (distraction phase). The rate at which the two bone segments are moved apart is slow enough so that new bone can form in the gap. When the desired length has been reached, a consolidation phase follows.

Whether in the long bones or in the craniofacial skeleton, distraction osteogenesis takes place primarily through intramembranous ossification. Histologic studies have identified 4 stages that result in the eventual formation of mature bone.

Stage I: The intervening gap initially is composed of fibrous tissue (longitudinally oriented collagen with spindle-shaped fibroblasts within a mesenchymal matrix of undifferentiated cells).

Stage II: Slender trabeculae of bone are observed extending from the bony edges. Early bone formation advances along collagen fibers with osteoblasts on the surface of these early bony spicules laying down bone matrix. Histochemically, significantly increased levels of alkaline phosphatase, pyruvic acid, and lactic acid are noted.

Stage III: Remodeling begins with advancing zones of bone apposition and resorption and an increase in the number of osteoclasts.

Stage IV: Early compact cortical bone is formed adjacent to the mature bone of the sectioned bone ends, with increasingly less longitudinally oriented bony spicules; this resembles the normal architecture.

Bone remodeling begins during the consolidation phase and continues over 1-2 years, eventually transforming the regenerated bone into a mature osseous structure similar in size and shape to the adjacent bone. Although the volume of new bone is comparable to that of adjacent bones, animal studies show that mineral content and radiodensity is approximately 30% less, as is the tensile strength of the regenerated segment.

Moreover, delayed consolidation following distraction is a troubling complication. When delayed consolidation occurs, removal of bone fixators is postponed and the risk of other complications, such as infection, is increased.

In view of the problems associated with consolidation and the resulting new bone structure, it would be desirable to provide alternative osteogenic regeneration systems for use in osteodistraction procedures. It would additionally be desirable to provide methods of using alternative osteogenic regeneration systems in osteodistraction procedures.

SUMMARY OF THE INVENTION

The present invention provides compositions and methods for stimulating osteogenesis during and/or following bone distraction. The present compositions facilitate and, in some embodiments, accelerate the bone consolidation phase following bone distraction.

In one aspect, a composition of the present invention for stimulating osteogenesis during and/or following bone distraction comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, from about 0.1 mg/ml to about 1.0 mg/ml, or about 0.3 mg/ml. The concentration of PDGF within the solution may be within any of the concentration ranges stated above.

In some embodiments of the present invention, PDGF comprises PDGF homodimers and heterodimers, including PDGF-AA, PDGF-BB, PDGF-AB, PDGF-CC, PDGF-DD, and mixtures and derivatives thereof. In some embodiments, PDGF comprises PDGF-BB. In another embodiment PDGF comprises a recombinant human (rh) PDGF such as recombinant human PDGF-BB (rhPDGF-BB).

In some embodiments of the present invention, PDGF comprises PDGF fragments. In some embodiments rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with a embodiment, the rhPDGF-BB comprises at least 50% of intact rhPDGF-B (1-109).

A biocompatible matrix, according to some embodiments of the present invention, comprises a bone scaffolding material. In some embodiments, a bone scaffolding material comprises calcium phosphate. Calcium phosphate, in some embodiments, comprises β-tricalcium phosphate. In some embodiments, a bone scaffolding material comprises collagen or other biocompatible polymeric materials.

In another aspect, the present invention provides a composition for stimulating osteogenesis during and/or following bone distraction comprising a PDGF solution disposed in a biocompatible matrix, wherein the biocompatible matrix comprises a bone scaffolding material and a biocompatible binder. The PDGF solution may have a concentration of PDGF as described above. A bone scaffolding material, in some embodiments, comprises a calcium phosphate. In some embodiments, a calcium phosphate comprises a β-tricalcium phosphate. Moreover, in some embodiments, a biocompatible binder comprises a material operable to promote adhesion between combined substances. A biocompatible binder, for example, can promote adhesion between particles of a scaffolding material in the formation of a biocompatible matrix. In some embodiments, for example, a biocompatible binder comprising collagen can promote adhesion between β-TCP particles of a scaffolding material.

In some embodiments, biocompatible matrices include calcium phosphate particles with or without biocompatible binders or bone allograft such as demineralized freeze-dried bone allograft (DFDBA), mineralized freeze-dried bone allograft (FDBA), or particulate demineralized bone matrix (DBM). In another embodiment, biocompatible matrices comprise bone allograft such as DFDBA, DBM, or other bone allograft materials including cortical bone shapes, such as blocks, wedges, cylinders, or particles, or cancellous bone particles of various shapes and sizes.

Moreover, a biocompatible binder, according to some embodiments of the present invention, comprises proteins, polysaccharides, nucleic acids, carbohydrates, synthetic polymers, or mixtures thereof. In some embodiments, a biocompatible binder comprises collagen. In another embodiment, a biocompatible binder comprises collagen, such as bovine collagen or human collagen.

In some embodiments of the present invention, compositions for stimulating osteogenesis during and/or following bone distraction further comprise at least one contrast agent. Contrast agents, according to some embodiments of the present invention, are substances operable to at least partially provide differentiation of two or more bodily tissues when imaged and can assist in placement of compositions described herein in sites of distraction. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)—N,N'-bis[2-hydroxy-1-(hydroxymethyl)-ethyl]-2,4,6-triiodo-5-lactamido isophthalamide (Iopamidol) and derivatives thereof.

The compositions of the invention may be for use in treating a bone during an osteodistraction procedure and/or for use in the manufacture of a medicament useful in treating a bone during an osteodistraction procedure. It is to be understood that the use of the composition may involve any of the compositions and/or methods as described herein. In one embodiment of the invention is the use of a composition comprising a PDGF solution and a biocompatible matrix, wherein the solution is disposed in the biocompatible matrix, in the preparation of a medicament useful for stimulating osteogenesis in an osteodistraction procedure. In one embodiment of the invention is the use of a composition comprising a PDGF solution and a biocompatible matrix, wherein the solution is disposed in the biocompatible matrix, in the preparation of a medicament useful for accelerating bone consolidation in an osteodistraction procedure.

In another aspect, the present invention provides a kit comprising a biocompatible matrix in a first package and a solution comprising PDGF in a second package. In some embodiments, the solution comprises a predetermined concentration of PDGF. The concentration of PDGF can be predetermined according to the nature of the osteodistraction procedure being performed. Moreover, the amount of biocompatible matrix provided by a kit can be dependent on the nature or classification of the osteodistraction procedure being performed. A syringe can facilitate disposition of the PDGF solution in the biocompatible matrix for application at a surgical site, such as a site of bone distraction.

The present invention additionally provides methods for producing compositions for promoting osteogenesis. In some embodiments, a method for producing a composition comprises providing a solution comprising PDGF, providing a biocompatible matrix, and disposing the solution in the biocompatible matrix.

The present invention additionally provides methods of treating a bone during an osteodistraction procedure, and methods of promoting and/or accelerating osteogenesis during and/or following bone distraction.

In some embodiments, a method for stimulating and/or accelerating osteogenesis comprises providing a composition comprising a PDGF solution disposed in a biocompatible matrix and applying an effective amount of the composition to at least one site of bone distraction. In some embodiments, the composition comprising a PDGF solution disposed in a biocompatible matrix is applied during bone distraction. When applied during the bone distraction, the composition may be applied to the site one or more (e.g. two, three, four, five, six, seven, eight, nine, ten or more) times during bone distraction. In other embodiments, the composition is applied after bone distraction. When applied after bone distraction, the composition may be applied to the site one or more (e.g. two, three, four, five, six, seven, eight, nine, ten or more) times after bone distraction. In some embodiments, an effective amount of the composition is applied during and after bone distraction.

In some embodiments, a method of stimulating osteogenesis comprises: applying an effective amount of a composition comprising a platelet-derived growth factor (PDGF) solution disposed in a biocompatible matrix to at least one site of bone distraction. In some embodiments, the composition is applied during the distraction phase of the osteodistraction procedure. In some embodiments, the composition is applied during the consolidation phase of the osteodistraction procedure. In some embodiments, the composition is applied during the distraction and consolidation phases of the osteodistraction procedure. In some embodiments, the method comprises accelerating bone consolidation following bone distraction. In some embodiments, the composition is applied to the site at least twice. In some embodiments, the biocompatible matrix comprises a porous calcium phosphate. In some embodiments, the calcium phosphate comprises β-TCP. In some embodiments, the calcium phosphate has interconnected pores. In some embodiments, the calcium phosphate has a porosity greater than about 40%. In some embodiments, the calcium phosphate consists of particles in a range of about 100 microns to about 5000 microns in size. In some embodiments, the calcium phosphate consists of particles in a range of about 100 microns to about 300 microns in size. In some embodiments, the biocompatible matrix is resorbable such that at least about 80% of the calcium phosphate is resorbed within about one year of being implanted. In some embodiments, the calcium phosphate is capable of absorbing an amount of the PDGF solution that is equal to at least about 25% of the weight of the calcium phosphate. In some embodiments, the biocompatible matrix comprises collagen. In some embodiments, the PDGF is present in the solution at a concentration of about 0.1 mg/ml to about 1.0 mg/ml. In some embodiments, the PDGF is present in the solution at a concentration of about 0.3 mg/ml. In some embodiments, the solution comprises a buffer. In some embodiments, the biocompatible matrix has a porosity that facilitates cell migration into the composition. In some embodiments, the biocompatible matrix comprises collagen and β-TCP in a ratio of about 20:80. In some embodiments, the composition is injectable.

In a further embodiment, a method for stimulating osteogenesis comprises accelerating bone consolidation following bone distraction, wherein accelerating comprises providing a composition comprising a PDGF solution disposed in a biocompatible matrix and applying the composition to a site of bone distraction.

The present invention also provides methods of accelerating bone union following bone distraction. In some embodiments, a method for accelerating bone union following bone distraction comprises providing a composition comprising a PDGF solution disposed in a biocompatible matrix and applying an effective amount of the composition to at least one site of bone distraction.

Moreover, the present invention provides methods of performing osteodistraction procedures. In some embodiments, a method of performing an osteodistraction procedure comprises (a) partitioning a bone into a first bone segment and a second bone segment, (b) moving at least one of the first and second bone segments to produce a space between the first and second bone segments, and (c) stimulating osteogenesis in the space, wherein stimulating osteogenesis comprises providing a composition comprising a PDGF solution disposed in a biocompatible matrix and at least partially applying an effective amount of the composition in the space. In some embodiments, steps (b) and (c) can be repeated as many times as necessary to lengthen the bone any desired amount.

In some embodiments, a method of performing an osteodistraction procedure comprises: (a) partitioning a bone into a first bone segment and a second bone segment; (b) moving at least one of the first and second bone segments to form a space between the first and second bone segments; and (c) stimulating osteogenesis in the space, wherein stimulating osteogenesis comprises applying an effective amount of a composition comprising a PDGF solution disposed in a biocompatible matrix to the space. In some embodiments, the method further comprises repeating steps (b) and (c) a number of times necessary to lengthen the bone a desired amount.

In various embodiments, the bone may be lengthened a total of at least about 1 mm, at least about 2 mm, at least about 3 mm, at least about 4 mm, at least about 5 mm, at least about 6 mm, at least about 8 mm, at least about 10 mm, at least about 12 mm, at least about 15 mm, at least about 20 mm, at least about 25 mm, at least about 30 mm, at least about 35 mm, at least about 50 mm, at least about 75 mm, at least about 100 mm, at least about 125 mm, at least about 150 mm, at least about 175 mm, at least about 200 mm. In various embodiments, the first and second bone segments are separated by at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm per distraction step (e.g. during step (b) above). In some embodiments, the first and second bone segments are separated by about 0.5 mm to about 1.5 mm per distraction step. In some embodiments, the first and second bone segments are separated by about 0.8 mm to about 1.2 mm per distraction step. In some embodiments, the first and second bone segments are separated by about 1 mm per distraction step. In various embodiments, at least 1, at least 2, at least 3, at least 4, at least 5, at least 10, at least 15, at least 20, at least 25 distraction steps may be performed.

In some embodiments of methods of the present invention, applying a composition comprising a PDGF solution disposed in a biocompatible matrix comprises injecting the composition in a site of bone distraction. In some embodiments, injecting comprises percutaneous injection of the composition in the distraction site. In another embodiment, the composition is injected into an open or surgically exposed site of bone distraction. In a further embodiment, applying the composition comprises disposing the composition in a site of bone distraction with a spatula or other device.

In some embodiments of the methods of the invention, the composition is applied to the distraction site once. In various embodiments, the composition is applied to the distraction site at least twice, at least three times, at least four times, at least five times, at least six times, at least eight times, at least ten times during the distraction and/or consolidation phases. In various embodiments, the composition may be administered to the distraction site more than once daily, daily, every other day, every third day, every fourth day, every fifth day, every six day, every week, or less than once per week during the distraction and/or consolidation phases.

In some embodiments of methods of the present invention, the biocompatible matrix comprises a bone scaffolding material. In some embodiments, the biocompatible matrix comprises a bone scaffolding material and a biocompatible binder.

As provided herein, in some embodiments, a composition of the present invention is applied to at least one site of bone distraction during the distraction phase of an osteodistraction procedure. In other embodiments, a composition of the present invention is applied to at least one site of bone distraction during the consolidation phase following bone distraction. In a further embodiment, a composition of the present invention is applied to at least one site of bone distraction during the distraction and consolidation phases.

As provided herein, osteodistraction procedures, according to some embodiments of the present invention, comprise those used in the treatment of bilateral mandibular hypoplasia, hemifacial microsomia, congenital short femur, fibular hemimelia, hemiatrophy, achondroplasia, neurofibromatosis, bow legs, growth plate fractures, bone defects, craniofacial applications, osteomyelitis, septic arthritis, and poliomyelitis. Moreover, osteodistraction procedures, according to some embodiments of the present invention, comprise those used in the treatment of various traumas. Traumas requiring osteodistraction procedures can comprise fractures to long bones of the body including the femur, tibia, fibula, humerous, and/or radius. Traumas requiring osteodistraction procedures can also include fractures to the craniofacial bones. In some embodiments, for example, osteodistraction procedures can be used to lengthen bone in preparation for use with a prosthesis.

Accordingly, it is an object of the present invention to provide methods and compositions comprising PDGF disposed in a biocompatible matrix useful in facilitating and, in some embodiments, accelerating osteogenesis at sites of bone distraction.

It is another object of the present invention to provide kits for constructing compositions comprising PDGF disposed in a biocompatible matrix, the compositions being useful in facilitating and, in some embodiments, accelerating bone consolidation following bone distraction.

These and other embodiments of the present invention are described in greater detail in the detailed description which follows. These and other objects, features, and advantages of the present invention will become apparent after review of the following detailed description of the disclosed embodiments and claims.

DETAILED DESCRIPTION

Figure 1:
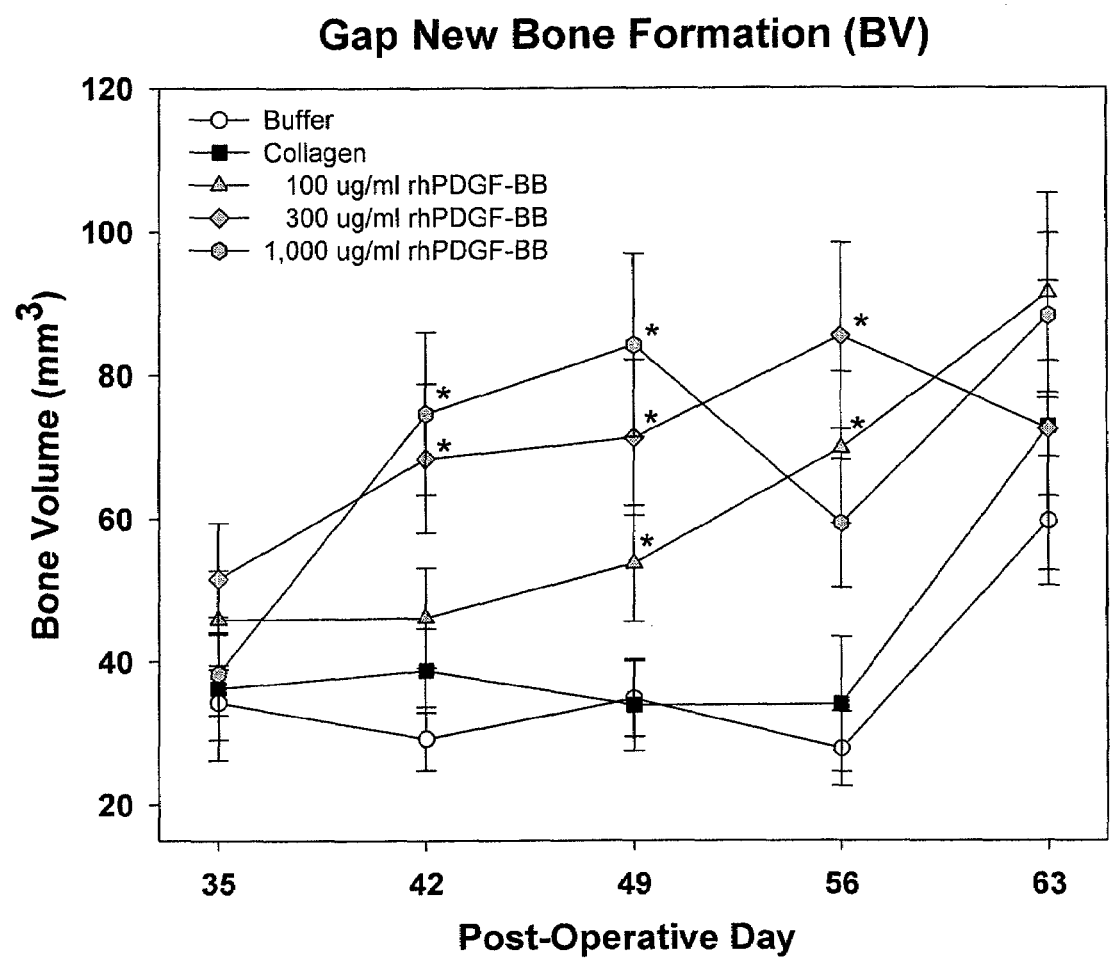
FIG. 1 illustrates volume of new bone formation in a distraction procedure as a function of composition administered and healing time according to one embodiment of the present invention.

The present invention provides compositions and methods for stimulating and/or accelerating osteogenesis during and/or following bone distraction. The present compositions facilitate and, in some embodiments, accelerate the bone union and the bone consolidation phase following bone distraction. In some embodiments, a composition comprises a solution comprising PDGF and a biocompatible matrix, wherein the solution is disposed in the biocompatible matrix. In another embodiment, a composition comprises a PDGF solution disposed in a biocompatible matrix, wherein the biocompatible matrix comprises a bone scaffolding material and a biocompatible binder.

Without wishing to be bound by theory, it is hypothesized that distraction osteogenesis is distinct from treating fractures, in that the bone segments are gradually moved apart during the distraction phase, thus re-injuring the site repeatedly, and thus keeping the new tissue in early stage bone healing during the distraction phase. During distraction, it is hypothesized that the state of the new tissue is soft, fibrous tissue callus (Phases I-III above), with some bone formation at the ends of the bones being distracted, and treatment of the distraction gap during the distraction phase of the procedure involves treating tissue during Phases I, II, and perhaps Phase III. Additionally, without wishing to be bound by theory, it is hypothesized that normal fracture healing occurs by endocortical ossification (which includes a cartilage intermediate), whereas distraction osteogenesis healing involves primarily intramembranous ossification (no cartilage intermediate).

Turning now to components that can be included in various embodiments of the present invention, compositions of the present invention comprise a solution comprising PDGF.

PDGF Solutions

PDGF plays an important role in regulating cell growth and migration. PDGF, as with other growth factors, is operable to bind with the extracellular domains of receptor tyrosine kinases. The binding of PDGF to these transmembrane proteins activates the kinase activity of their catalytic domains located on the cytosolic side of the membrane. By phosphorylating tyrosine residues of target proteins, the kinases induce a variety of cellular processes that include cell growth and extracellular matrix production.

In one aspect, a composition provided by the present invention comprises a solution comprising platelet derived growth factor (PDGF) and a biocompatible matrix, wherein the solution is disposed in the biocompatible matrix. In some embodiments, PDGF is present in the solution in a concentration ranging from about 0.01 mg/ml to about 10 mg/ml, from about 0.05 mg/ml to about 5 mg/ml, or from about 0.1 mg/ml to about 1.0 mg/ml. PDGF may be present in the solution at any concentration within these stated ranges. In various embodiments, PDGF is present in the solution at any one of the following concentrations: about 0.05 mg/ml; about 0.1 mg/ml; about 0.15 mg/ml; about 0.2 mg/ml; about 0.25 mg/ml; about 0.3 mg/ml; about 0.35 mg/ml; about 0.4 mg/ml; about 0.45 mg/ml; about 0.5 mg/ml, about 0.55 mg/ml, about 0.6 mg/ml, about 0.65 mg/ml, about 0.7 mg/ml; about 0.75 mg/ml; about 0.8 mg/ml; about 0.85 mg/ml; about 0.9 mg/ml; about 0.95 mg/ml; about 1.0 mg/ml; or about 3.0 mg/ml. In some embodiments, PDGF is present in the solution in a concentration ranging from about 0.2 mg/ml to about 2 mg/ml, from about 0.3 mg/ml to about 3 mg/ml, from about 0.4 mg/ml to about 4 mg/ml, from about 0.5 mg/ml to about 5 mg/ml, from about 0.25 mg/ml to about 0.5 mg/ml, or from about 0.2 mg/ml to about 0.75 mg/ml. It is to be understood that these concentrations are simply examples of particular embodiments, and that the concentration of PDGF may be within any of the concentration ranges stated above.

Various amounts of PDGF may be used in the compositions of the present invention. Amounts of PDGF that could be used include amounts in the following ranges: about 1 ug to about 50 mg, about 10 ug to about 25 mg, about 100 ug to about 10 mg, and about 250 ug to about 5 mg.

The concentration of PDGF or other growth factors in embodiments of the present invention can be determined by using an enzyme-linked immunoassay as described in U.S. Pat. Nos. 6,221,625, 5,747,273, and 5,290,708, or any other assay known in the art for determining PDGF concentration. When provided herein, the molar concentration of PDGF is determined based on the molecular weight of PDGF dimer (e.g., PDGF-BB; MW about 25 kDa).

In embodiments of the present invention, PDGF comprises PDGF homodimers and heterodimers, including PDGF-AA, PDGF-BB, PDGF-AB, PDGF-CC, PDGF-DD, and mixtures and derivatives thereof. In some embodiments, PDGF comprises PDGF-BB. In another embodiment PDGF comprises a recombinant human PDGF, such as rhPDGF-BB. In some embodiments, PDGF comprises mixtures of the various homodimers and/or heterodimers. Embodiments of the present invention contemplate any combination of PDGF-AA, PDGF-BB, PDGF-AB, PDGF-CC, and/or PDGF-DD PDGF, in some embodiments, can be obtained from natural sources. In other embodiments, PDGF can be produced by recombinant DNA techniques. In other embodiments, PDGF or fragments thereof may be produced using peptide synthesis techniques known to one of ordinary skill in the art, such as solid phase peptide synthesis. When obtained from natural sources, PDGF can be derived from biological fluids. Biological fluids, according to some embodiments, can comprise any treated or untreated fluid associated with living organisms including blood.

Biological fluids, in another embodiment, can also comprise blood components including platelet concentrate (PC), apheresed platelets, platelet-rich plasma (PRP), plasma, serum, fresh frozen plasma (FFP), and buffy coat (BC). Biological fluids, in a further embodiment, can comprise platelets separated from plasma and resuspended in a physiological fluid.

When produced by recombinant DNA techniques, a DNA sequence encoding a single monomer (e.g., PDGF B-chain or A-chain), in some embodiments, can be inserted into cultured prokaryotic or eukaryotic cells for expression to subsequently produce the homodimer (e.g. PDGF-BB or PDGF-AA). In other embodiments, a PDGF heterodimer can be generated by inserting DNA sequences encoding for both monomeric units of the heterodimer into cultured prokaryotic or eukaryotic cells and allowing the translated monomeric units to be processed by the cells to produce the heterodimer (e.g. PDGF-AB). Commercially available cGMP recombinant PDGF-BB can be obtained commercially from Novartis Corporation (Emeryville, Calif.). Research grade rhPDGF-BB can be obtained from multiple sources including R&D Systems, Inc. (Minneapolis, Minn.), BD Biosciences (San Jose, Calif.), and Chemicon, International (Temecula, Calif.). In some embodiments, monomeric units can be produced in prokaryotic cells in a denatured form, wherein the denatured form is subsequently refolded into an active molecule.

In embodiments of the present invention, PDGF comprises PDGF fragments. In some embodiments rhPDGF-B comprises the following fragments: amino acid sequences 1-31, 1-32, 33-108, 33-109, and/or 1-108 of the entire B chain. The complete amino acid sequence (1-109) of the B chain of PDGF is provided in FIG. 15 of U.S. Pat. No. 5,516,896. It is to be understood that the rhPDGF compositions of the present invention may comprise a combination of intact rhPDGF-B (1-109) and fragments thereof. Other fragments of PDGF may be employed such as those disclosed in U.S. Pat. No. 5,516,896. In accordance with one embodiment, the rhPDGF-BB comprises at least about 60% of intact rhPDGF-B (1-109). In another embodiment, the rhPDGF-BB comprises at least about 65%, 75%, 80%, 85%, 90%, 95% or 99% of intact rhPDGF-B (1-109).

In some embodiments of the present invention, PDGF can be purified. Purified PDGF, as used herein, comprises compositions having greater than about 95% by weight PDGF prior to incorporation in solutions of the present invention. The solution may be any pharmaceutically acceptable solution. In other embodiments, the PDGF can be substantially purified. Substantially purified PDGF, as used herein, comprises compositions having about 5% to about 95% by weight PDGF prior to incorporation into solutions of the present invention. In some embodiments, substantially purified PDGF comprises compositions having about 65% to about 95% by weight PDGF prior to incorporation into solutions of the present invention. In other embodiments, substantially purified PDGF comprises compositions having about 70% to about 95%, about 75% to about 95%, about 80% to about 95%, about 85% to about 95%, or about 90% to about 95%, by weight PDGF, prior to incorporation into solutions of the present invention. Purified PDGF and substantially purified PDGF may be incorporated into scaffolds and binders.

In a further embodiment, PDGF can be partially purified. Partially purified PDGF, as used herein, comprises compositions having PDGF in the context of platelet rich plasma (PRP), fresh frozen plasma (FFP), or any other blood product that requires collection and separation to produce PDGF. Embodiments of the present invention contemplate that any of the PDGF isoforms provided herein, including homodimers and heterodimers, can be purified or partially purified. Compositions of the present invention containing PDGF mixtures may contain PDGF isoforms or PDGF fragments in partially purified proportions. Partially purified and purified PDGF, in some embodiments, can be prepared as described in U.S. patent application Ser. No. 11/159,533 (Publication No: 20060084602).

In some embodiments, solutions comprising PDGF are formed by solubilizing PDGF in one or more buffers. Buffers suitable for use in PDGF solutions of the present invention can comprise, but are not limited to, carbonates, phosphates (e.g. phosphate buffered saline), histidine, acetates (e.g. sodium acetate), acidic buffers such as acetic acid and HCl, and organic buffers such as lysine, Tris buffers (e.g. tris(hydroxymethyl)aminoethane), N-2-hydroxyethylpiperazine-N'-2-ethanesulfonic acid (HEPES), and 3-(N-morpholino)propanesulfonic acid (MOPS). Buffers can be selected based on biocompatibility with PDGF and the buffer's ability to impede undesirable protein modification. Buffers can additionally be selected based on compatibility with host tissues. In some embodiments, sodium acetate buffer is used. The buffers may be employed at different molarities, for example about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer (e.g. sodium acetate) is employed at a molarity of about 20 mM.

In another embodiment, solutions comprising PDGF are formed by solubilizing lyophilized PDGF in water, wherein prior to solubilization the PDGF is lyophilized from an appropriate buffer.

Solutions comprising PDGF, according to embodiments of the present invention, can have a pH ranging from about 3.0 to about 8.0. In some embodiments, a solution comprising PDGF has a pH ranging from about 5.0 to about 8.0, more preferably about 5.5 to about 7.0, most preferably about 5.5 to about 6.5, or any value within these ranges. In some embodiments, the pH is about 6.0. The pH of solutions comprising PDGF, in some embodiments, can be compatible with the prolonged stability and efficacy of PDGF or any other desired biologically active agent. PDGF is generally more stable in an acidic environment. Therefore, in accordance with one embodiment the present invention comprises an acidic storage formulation of a PDGF solution. In accordance with this embodiment, the PDGF solution preferably has a pH from about 3.0 to about 7.0, and more preferably from about 4.0 to about 6.5. The biological activity of PDGF, however, can be optimized in a solution having a neutral pH range. Therefore, in a further embodiment, the present invention comprises a neutral pH formulation of a PDGF solution. In accordance with this embodiment, the PDGF solution preferably has a pH from about 5.0 to about 8.0, more preferably about 5.5 to about 7.0, most preferably about 5.5 to about 6.5. In accordance with a method of the present invention, an acidic PDGF solution is reformulated to a neutral pH composition, wherein such composition is then used to promote bone growth at distraction sites in osteodistraction procedures. In accordance with one embodiment of the present invention, the PDGF utilized in the solutions is rhPDGF-BB.

In some embodiments, the pH of the PDGF containing solution may be altered to optimize the binding kinetics of PDGF to a matrix substrate or linker. If desired, as the pH of the material equilibrates to adjacent material, the bound PDGF may become labile.

The pH of solutions comprising PDGF, in some embodiments, can be controlled by the buffers recited herein. Various proteins demonstrate different pH ranges in which they are stable. Protein stabilities are primarily reflected by isoelectric points and charges on the proteins. The pH range can affect the conformational structure of a protein and the susceptibility of a protein to proteolytic degradation, hydrolysis, oxidation, and other processes that can result in modification to the structure and/or biological activity of the protein.

In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N,N,N', N'-tetraacetic acid (EGTA), aprotinin, $\epsilon$-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), hepatocyte growth factors (HGFs), bone morphogenetic proteins (BMPs), or other PDGFs including compositions of PDGF-AA, PDGF-BB, PDGF-AB, PDGF-CC and/or PDGF-DD.

In addition to solutions comprising PDGF, compositions of the present invention also comprise a biocompatible matrix in which to dispose the PDGF solutions and may also comprise a biocompatible binder either with or without a biocompatible matrix.

Biocompatible Matrix

Scaffolding Material

A biocompatible matrix, according to embodiments of the present invention, comprises a scaffolding material. The scaffolding material, according to embodiments of the present invention, provides the framework or scaffold for new tissue and/or bone growth to occur. A scaffolding material, in some embodiments, comprises multi-directional and interconnected pores of varying diameters. In some embodiments, a scaffolding material comprises a plurality of pockets and non-interconnected pores of various diameters in addition to the interconnected pores.

A scaffolding material, in some embodiments, comprises at least one calcium phosphate. In other embodiments, a scaffolding material can comprise a plurality of calcium phosphates. Calcium phosphates suitable for use as a scaffolding material, in some embodiments of the present invention, have a calcium to phosphorus atomic ratio ranging from 0.5 to 2.0. In some embodiments, the biocompatible matrix comprises allograft such as demineralized freeze-dried bone allograft (DFDBA), particulate demineralized bone matrix (DBM), mineralized bone matrix, or combinations thereof.

Non-limiting examples of calcium phosphates suitable for use as scaffolding materials comprise amorphous calcium phosphate, monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), α-tricalcium phosphate, β-tricalcium phosphate, hydroxyapatite (OHAp), poorly crystalline hydroxyapatite, tetracalcium phosphate (TTCP), heptacalcium decaphosphate, calcium metaphosphate, calcium pyrophosphate dihydrate, carbonated calcium phosphate, calcium pyrophosphate, hydroxyapatite, or derivatives thereof.

In some embodiments, a scaffolding material comprises a polymeric material. A polymeric scaffold, in some embodiments, comprises collagen, polylactic acid, poly(L-lactide), poly(D,L-lactide), polyglycolic acid, poly(L-lactide-co-glycolide), poly(L-lactide-co-D,L-lactide), polyacrylate, polymethacrylate, polymethylmethacrylate, chitosan, or combinations or derivatives thereof.

In some embodiments, a scaffolding material comprises porous structure. Porous scaffolding materials, according to some embodiments, can comprise pores having diameters ranging from about 1 μm to about 1 mm. In some embodiments, a scaffolding material comprises macropores having diameters ranging from about 100 μm to about 1 mm or greater. In another embodiment, a scaffolding material comprises mesopores having diameters ranging from about 10 μm to about 100 μm. In a further embodiment, a scaffolding material comprises micropores having diameters less than about 10 μm. Embodiments of the present invention contemplate scaffolding materials comprising macropores, mesopores, and micropores or any combination thereof.

A porous scaffolding material, in some embodiments, has a porosity greater than about 25% or greater than about 40%. In another embodiment, a porous scaffolding material has a porosity greater than about 50%, greater than about 60%, greater than about 65%, greater than about 70%, greater than about 80%, or greater than about 85%. In a further embodiment, a porous scaffolding material has a porosity greater than about 90%. In some embodiments, a porous scaffolding material comprises a porosity that facilitates cell migration into the scaffolding material.

In some embodiments, a scaffolding material comprises a plurality of particles. Scaffolding particles may be mm, μm, or submicron (nm) in size. Scaffolding particles, in some embodiments, have an average diameter ranging from about 1 μm to about 5 mm. In other embodiments, particles have an average diameter ranging from about 1 mm to about 2 mm, from about 1 mm to about 3 mm, or from about 250 μm to about 750 μm. Scaffolding particles, in another embodiment, have an average diameter ranging from about 100 μm to about 300 μm. In a further embodiment, scaffolding particles have an average diameter ranging from about 75 μm to about 300 μm. In additional embodiments, scaffolding particles have an average diameter less than about 25 μm, less than about 1 μm, or less than about 1 mm. In some embodiments, scaffolding particles have an average diameter ranging from about 100 μm to about 5 mm or from about 100 μm to about 3 mm. In other embodiments, scaffolding particles have an average diameter ranging from about 250 μm to about 2 mm, from about 250 μm to about 1 mm, or from about 200 μm to about 3 mm. Particles may also be in the range of about 1 nm to about 1 μm, less than about 500 nm, or less than about 250 nm.

Scaffolding materials, according to some embodiments, are moldable, extrudable and/or injectable. Moldable, extrudable, and/or injectable scaffolding materials can facilitate efficient placement of compositions of the present invention in and around sites of bone distraction. In some embodiments, moldable, extrudable, and/or injectable scaffolding materials are applied to sites of bone distraction with a spatula or equivalent device. In some embodiments, scaffolding materials are flowable. Flowable scaffolding materials, in some embodiments, can be applied to a site of bone distraction through a syringe and needle or cannula. In some embodiments, the flowable scaffolding materials can be applied to a site of bone distraction percutaneously. In other embodiments, flowable scaffolding materials can be applied to a surgically exposed site of bone distraction. Moreover, in some embodiments, scaffolding materials are provided as blocks or particles.

In some embodiments, scaffolding materials are bioresorbable. A scaffolding material, in some embodiments, can be at least about 30%, 40%, 50%, 60%, 70%, 75%, 80%, 85%, or 90% resorbed within one year subsequent to in vivo implantation. In another embodiment, a scaffolding material can be resorbed at least about 5%, 10%, 20%, 30%, 40%, 50%, 60%, 70%, 75%, 80%, 85% or 90% within about 1, 3, 6, 9, 12, or 18 months of in vivo implantation. In some embodiments, scaffolding materials are greater than 90% resorbed within about 1, 3, 6, 9, 12, or 18 months of in vivo implantation. Bioresorbability will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Scaffolding Comprising β-Tricalcium Phosphate

A scaffolding material for use as a biocompatible matrix, in some embodiments, comprises β-tricalcium phosphate (β-TCP). β-TCP, according to some embodiments, can comprise a porous structure having multidirectional and interconnected pores of varying diameters. In some embodiments, β-TCP comprises a plurality of pockets and non-interconnected pores of various diameters in addition to the interconnected pores. The porous structure of β-TCP, in some embodiments, comprises macropores having diameters ranging from about 100 µm to about 1 mm or greater, mesopores having diameters ranging from about 10 µm to about 100 µm, and micropores having diameters less than about 10 µm. Macropores and mesopores of the β-TCP can facilitate tissue in-growth including osteoinduction and osteoconduction while macropores, mesopores and micropores can permit fluid communication and nutrient transport to support tissue and bone regrowth, throughout the β-TCP biocompatible matrix.

In comprising a porous structure, β-TCP, in some embodiments, can have a porosity greater than about 25%, or greater than about 40%. In other embodiments, β-TCP can have a porosity greater than about 50%, greater than about 60%, greater than about 65%, greater than about 70%, greater than about 75%, greater than about 80%, or greater than about 85%. In a further embodiment, β-TCP can have a porosity greater than about 90%. In some embodiments, β-TCP can have a porosity that facilitates cell migration into the β-TCP.

In some embodiments, a scaffolding material comprises β-TCP particles. β-TCP particles, in some embodiments, can individually demonstrate any of the pore diameters, pore structures, and porosities provided herein for scaffolding materials.

β-TCP particles, in some embodiments have an average diameter ranging from about 1 µm to about 5 mm. In other embodiments, β-TCP particles have an average diameter ranging from about 1 mm to about 2 mm, from about 1 mm to about 3 mm, from about 100 µm to about 5 mm, from about 100 µm to about 3 mm, from about 250 µm to about 2 mm, from about 250 µm to about 750 µm, from about 250 µm to about 1 mm, from about 250 µm to about 2 mm, or from about 200 µm to about 3 mm. In another embodiment, β-TCP particles have an average diameter ranging from about 100 µm to about 300 µm. In some embodiments, β-TCP particles have an average diameter ranging from about 75 µm to about 300 µm. In some embodiments, β-TCP particles have an average diameter of less than about 25 µm, less than about 1 µm, or less than about 1 mm. In some embodiments, β-TCP particles have an average diameter ranging from about 1 nm to about 1 µm. In a further embodiment, β-TCP particles have an average diameter less than about 500 nm or less than about 250 nm.

A biocompatible matrix comprising β-TCP particles, in some embodiments, can be provided in a shape suitable for implantation (e.g., a sphere, a cylinder, or a block). In other embodiments, a β-TCP scaffolding material is moldable, extrudable, and/or injectable thereby facilitating application of the matrix to sites of bone distraction. Flowable matrices may be applied through syringes, tubes, cannulas, or spatulas.

A β-TCP scaffolding material, according to some embodiments, is bioresorbable. In some embodiments, a β-TCP scaffolding material can be at least about 30%, 40%, 50%, 60%, 65%, 70%, 75%, 80%, or 85% resorbed about one year subsequent to in vivo implantation. In another embodiment, a β-TCP scaffolding material can be greater than about 90% resorbed about one year subsequent to in vivo implantation.

Scaffolding Material and Biocompatible Binder

In another embodiment, a biocompatible matrix comprises a scaffolding material and a biocompatible binder.

Biocompatible binders, according to some embodiments, can comprise materials operable to promote cohesion between combined substances. A biocompatible binder, for example, can promote adhesion between particles of a scaffolding material in the formation of a biocompatible matrix. In certain embodiments, the same material may serve as both a scaffolding material and binder. In some embodiments, for example, polymeric materials described herein such as collagen and chitosan may serve as both a scaffolding material and a binder.

Biocompatible binders, in some embodiments, can comprise collagen, elastin, polysaccharides, nucleic acids, carbohydrates, proteins, polypeptides, poly(α-hydroxy acids), poly(lactones), poly(amino acids), poly(anhydrides), polyurethanes, poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D,L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers and mixtures thereof.

Biocompatible binders, in other embodiments, can comprise alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, lecithin, phosphatidylcholine derivatives, glycerol, hyaluronic acid, sodium hyaluronate, a cellulose (e.g., methylcellulose, carboxymethylcellulose, hydroxypropyl methylcellulose, or hydroxyethyl cellulose), a glucosamine, a proteoglycan, a starch (e.g., hydroxyethyl starch or starch soluble), lactic acid, pluronic acids, sodium glycerophosphate, glycogen, a keratin, silk, and derivatives and mixtures thereof.

In some embodiments, a biocompatible binder is water-soluble. A water-soluble binder can dissolve from the biocompatible matrix shortly after its implantation, thereby introducing macroporosity into the biocompatible matrix. Macroporosity, as discussed herein, can increase the osteoconductivity of the implant material by enhancing the access and, consequently, the remodeling activity of the osteoclasts and osteoblasts at the implant site.

In some embodiments, a biocompatible binder can be present in a biocompatible matrix in an amount ranging from about 5 weight percent to about 50 weight percent of the matrix. In other embodiments, a biocompatible binder can be present in an amount ranging from about 10 weight percent to about 40 weight percent of the biocompatible matrix. In another embodiment, a biocompatible binder can be present in an amount ranging from about 15 weight percent to about 35 weight percent of the biocompatible matrix. In a further embodiment, a biocompatible binder can be present in an amount of about 20 weight percent of the biocompatible matrix. In another embodiment, a biocompatible binder can be present in a biocompatible matrix in an amount greater than about 50 weight percent or 60 weight percent of the matrix. In some embodiments, a biocompatible binder can be present in a biocompatible matrix in an amount up to about 99 weight percent of the matrix.

A biocompatible matrix comprising a scaffolding material and a biocompatible binder, according to some embodiments, can be flowable, moldable, and/or extrudable. In such embodiments, a biocompatible matrix can be in the form of a paste or putty. A biocompatible matrix in the form of a paste or putty, in some embodiments, can comprise particles of a scaffolding material adhered to one another by a biocompatible binder.

A biocompatible matrix in paste or putty form can be molded into the desired implant shape or can be molded to the contours of the implantation site. In some embodiments, a biocompatible matrix in paste or putty form can be injected into an implantation site with a syringe or cannula.

In some embodiments, a biocompatible matrix in paste or putty form does not harden and retains a flowable and moldable form subsequent to implantation. In other embodiments, a paste or putty can harden subsequent to implantation, thereby reducing matrix flowability and moldability.

A biocompatible matrix comprising a scaffolding material and a biocompatible binder, in some embodiments, is bioresorbable. A biocompatible matrix, in such embodiments, can be resorbed within about one year of in vivo implantation. In another embodiment, a biocompatible matrix comprising a scaffolding material and a biocompatible binder can be resorbed within about 1, 3, 6, or 9 months of in vivo implantation. In some embodiments, a biocompatible matrix comprising a scaffolding material and a biocompatible binder can be resorbed within about 1, 3, or 6 years of in vivo implantation. Bioresorbablity will be dependent on: (1) the nature of the matrix material (i.e., its chemical make up, physical structure and size); (2) the location within the body in which the matrix is placed; (3) the amount of matrix material that is used; (4) the metabolic state of the patient (diabetic/non-diabetic, osteoporotic, smoker, old age, steroid use, etc.); (5) the extent and/or type of injury treated; and (6) the use of other materials in addition to the matrix such as other bone anabolic, catabolic and anti-catabolic factors.

Biocompatible Matrix Comprising, β-TCP and Collagen

In some embodiments, a biocompatible matrix can comprise a β-TCP scaffolding material and a biocompatible collagen binder. β-TCP scaffolding materials suitable for combination with a collagen binder are consistent with those provided hereinabove.

A collagen binder, in some embodiments, comprises any type of collagen, including Type I, Type II, and Type III collagens. In some embodiments, a collagen binder comprises a mixture of collagens, such as a mixture of Type I and Type II collagen. In other embodiments, a collagen binder is soluble under physiological conditions. Other types of collagen present in bone or musculoskeletal tissues may be employed. Recombinant, synthetic and naturally occurring forms of collagen may be used in the present invention.

A biocompatible matrix, according to some embodiments, can comprise a plurality of β-TCP particles adhered to one another with a collagen binder. In some embodiments, β-TCP particles for combination with a collagen binder have an average diameter ranging from about 1 μm to about 5 mm. In other embodiments, β-TCP particles have an average diameter ranging from about 1 mm to about 2 mm, from about 1 mm to about 3 mm, from about 100 μm to about 5 mm, from about 100 μm to about 3 mm, from about 250 μm to about 2 mm, from about 250 μm to about 750 μm, from about 250 μm to about 1 mm, from about 250 μm to about 2 mm, or from about 200 μm to about 3 mm. In another embodiment, β-TCP particles have an average diameter ranging from about 100 μm to about 300 μm. In some embodiments, β-TCP particles have an average diameter ranging from about 75 μm to about 300 μm. In some embodiments, β-TCP particles have an average diameter of less than about 25 μm, less than about 1 μm, or less than about 1 mm. In some embodiments, β-TCP particles have an average diameter ranging from about 1 nm to about 1 μm. In a further embodiment, β-TCP particles have an average diameter less than about 500 nm or less than about 250 nm.

β-TCP particles, in some embodiments, can be adhered to one another by the collagen binder so as to produce a biocompatible matrix having a porous structure. In some embodiments, the porous structure of a biocompatible matrix comprising β-TCP particles and a collagen binder demonstrates multidirectional and interconnected pores of varying diameters. In some embodiments, a the biocompatible matrix comprises a plurality of pockets and non-interconnected pores of various diameters in addition to the interconnected pores.

In some embodiments, a biocompatible matrix comprising β-TCP particles and a collagen binder can comprise pores having diameters ranging from about 1 μm to about 1 mm. A biocompatible matrix comprising β-TCP particles and a collagen binder can comprise macropores having diameters ranging from about 100 μm to about 1 mm or greater, mesopores having diameters ranging from about 10 μm to about 100 μm, and micropores having diameters less than about 10 μm.

A biocompatible matrix comprising β-TCP particles and a collagen binder can have a porosity greater than about 25%, or greater than about 40%. In various embodiments, the biocompatible matrix can have a porosity greater than about 50%, greater than about 65%, greater than about 70%, greater than about 75%, greater than about 80%, or greater than about 85%. In a further embodiment, the biocompatible matrix can have a porosity greater than about 90%. In some embodiments, the biocompatible matrix can have a porosity that facilitates cell migration into the matrix.

In some embodiments, the β-TCP particles, can individually demonstrate any of the pore diameters, pore structures, and porosities provided herein for a biocompatible matrix comprising the β-TCP and collagen binder.

A biocompatible matrix comprising β-TCP particles, in some embodiments, can comprise a collagen binder in an amount ranging from about 5 weight percent to about 50 weight percent of the matrix. In other embodiments, a collagen binder can be present in an amount ranging from about 10 weight percent to about 40 weight percent of the biocompatible matrix. In another embodiment, a collagen binder can be present in an amount ranging from about 15 weight percent to about 35 weight percent of the biocompatible matrix. In a further embodiment, a collagen binder can be present in an amount of about 20 weight percent of the biocompatible matrix. In another embodiment, a collagen binder is present in an amount of about 20 weight percent of the biocompatible matrix, and β-TCP is present in an amount of about 80 weight percent of the biocompatible matrix. In some embodiments, the collagen is soluble bovine type I collagen. In some embodiments, the β-TCP comprises granules having a diameter of about 100 to about 300 microns.

In some embodiments, the biocompatible matrix is composed of 20% soluble bovine type I collagen and 80% β-TCP granules (100-300 micron particle diameter range) by mass. In some embodiments, the matrix is combined with a liquid formulation of 0.3 mg/ml rhPDGF-BB in 20 mM sodium acetate solution, pH 6.0, and the two components mixed to generate a paste that can be injected or spread over a bone surface.

A biocompatible matrix comprising β-TCP particles and a collagen binder, according to some embodiments, can be flowable, moldable, and/or extrudable. In such embodiments, the biocompatible matrix can be in the form of a paste or putty. A paste or putty can be molded into the desired implant shape or can be molded to the contours of the implantation site. In some embodiments, a biocompatible matrix in paste or putty form comprising β-TCP particles and a collagen binder can be injected into an implantation site with a syringe or cannula. In various embodiments, the biocompatible matrix comprising β-TCP particles and a collagen binder can be injected into an implantation site through e.g. a 10, 11, 12, 13, 14, 15, 16, 17, 18, 19, or 20 gauge needle.

In some embodiments, a biocompatible matrix in paste or putty form comprising β-TCP particles and a collagen binder can retain a flowable and moldable form when implanted. In other embodiments, the paste or putty can harden subsequent to implantation, thereby reducing matrix flowability and moldability.

A biocompatible matrix comprising β-TCP particles and a collagen binder, in some embodiments, can be provided in a predetermined shape such as a block, sphere, or cylinder.

A biocompatible matrix comprising β-TCP particles and a collagen binder can be resorbable. In some embodiments, a biocompatible matrix comprising β-TCP particles and a collagen binder can be at least about 75% resorbed about one year subsequent to in vivo implantation. In another embodiment, a biocompatible matrix comprising β-TCP particles and a collagen binder can be greater than about 90% resorbed about one year subsequent to in vivo implantation.

In some embodiments, a solution comprising PDGF can be disposed in a biocompatible matrix to produce a composition for use in osteodistraction procedures.

Disposing a PDGF Solution in a Biocompatible Matrix

The present invention provides methods for producing compositions for stimulating osteogenesis during and/or following bone distraction. In some embodiments, a method for producing such compositions comprises providing a solution comprising PDGF, providing a biocompatible matrix, and disposing the solution in the biocompatible matrix. PDGF solutions and biocompatible matrices suitable for combination are consistent with those described hereinabove.

In some embodiments, a PDGF solution can be disposed in a biocompatible matrix by soaking the biocompatible matrix in the PDGF solution. A PDGF solution, in another embodiment, can be disposed in a biocompatible matrix by injecting the biocompatible matrix with the PDGF solution. In some embodiments, injecting a PDGF solution can comprise disposing the PDGF solution in a syringe and expelling the PDGF solution into the biocompatible matrix to saturate the biocompatible matrix.

In some embodiments, the PDGF is absorbed into the pores of the biocompatible matrix. In some embodiments, the PDGF is adsorbed onto one or more surfaces of the biocompatible matrix, including surfaces within pores of the biocompatible matrix.

In some embodiments, the biocompatible matrix is capable of absorbing an amount of liquid comprising PDGF that is equal to at least about 25% of the weight of the biocompatible matrix. In various embodiments, the biocompatible matrix is capable of absorbing an amount of liquid comprising PDGF that is equal to at least about 50%, at least about 200%, at least about 300% of the weight of the biocompatible matrix.

The biocompatible matrix, according to some embodiments, can be in a predetermined shape, such as a brick or cylinder, prior to receiving a PDGF solution. Subsequent to receiving a PDGF solution, the biocompatible matrix can have a paste or putty form that is flowable, extrudable, and/or injectable. In other embodiments, the biocompatible matrix can demonstrate a flowable, extrudable, and/or injectable paste or putty form prior to receiving a solution comprising PDGF.

Compositions Further Comprising Biologically Active Agents

Compositions of the present invention, according to some embodiments, can further comprise one or more biologically active agents in addition to PDGF. Biologically active agents that can be incorporated into compositions of the present invention, in addition to PDGF, can comprise organic molecules, inorganic materials, proteins, peptides, nucleic acids (e.g., genes, gene fragments, small-interfering ribonucleic acids [si-RNAs] gene regulatory sequences, nuclear transcriptional factors, and antisense molecules), nucleoproteins, polysaccharides (e.g., heparin), glycoproteins, and lipoproteins. Non-limiting examples of biologically active compounds that can be incorporated into compositions of the present invention, including, e.g., anti-cancer agents, antibiotics, analgesics, anti-inflammatory agents, immunosuppressants, enzyme inhibitors, antihistamines, hormones, muscle relaxants, prostaglandins, trophic factors, osteoinductive proteins, growth factors, and vaccines, are disclosed in U.S. patent application Ser. No. 11/159,533 (Publication No: 20060084602). Biologically active compounds that can be incorporated into compositions of the present invention include osteostimulatory factors such as insulin-like growth factors, fibroblast growth factors, or other PDGFs. In accordance with other embodiments, biologically active compounds that can be incorporated into compositions of the present invention preferably include osteoinductive and osteostimulatory factors such as bone morphogenetic proteins (BMPs), BMP mimetics, calcitonin, or calcitonin mimetics, statins, statin derivatives, fibroblast growth factors, insulin-like growth factors, growth-differentiating factors, small molecule or antibody blockers of Wnt antagonists (e.g. sclerostin, DKK, soluble Wnt receptors), and parathyroid hormone. In some embodiments, factors also include protease inhibitors, as well as osteoporotic treatments that decrease bone resorption including bisphosphonates, teriparadide, and antibodies to the activator receptor of the NF-kB (RANK) ligand.

Standard protocols and regimens for delivery of additional biologically active agents are known in the art. Additional biologically active agents can be introduced into compositions of the present invention in amounts that allow delivery of an appropriate dosage of the agent to the implant site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the bioresorbability of the biocompatible matrix. Standard clinical trials may be used to optimize the dose and dosing frequency for any particular additional biologically active agent.

A composition of the present invention, according to some embodiments, can further comprise the addition of additional grafting materials with PDGF including autologous bone marrow, autologous platelet extracts, allografts, synthetic bone matrix materials, xenografts, and derivatives thereof.

In some embodiments of the present invention, compositions for stimulating osteogenesis during and/or following bone distraction further comprise at least one contrast agent. Contrast agents, according to embodiments of the present invention, are substances operable to at least partially provide differentiation of two or more bodily tissues when imaged. Contrast agents, according to some embodiments, comprise cationic contrast agents, anionic contrast agents, nonionic contrast agents, or mixtures thereof. In some embodiments, contrast agents comprise radiopaque contrast agents. Radiopaque contrast agents, in some embodiments, comprise iodo-compounds including (S)—N,N'-bis[2-hydroxy-1-(hydroxymethyl)-ethyl]-2,4,6-triiodo-5-lactamidoisophthalamide (lopamidol) and derivatives thereof.

Methods of Stimulating Osteogenesis

In some embodiments, a method for stimulating and/or accelerating osteogenesis comprises providing a composition comprising a PDGF solution disposed in a biocompatible matrix and applying an effective amount of the composition to at least one site of bone distraction. In some embodiments, the composition comprising a PDGF solution disposed in a biocompatible matrix is applied during bone distraction. In other embodiments, the composition is applied after bone distraction. In some embodiments, an effective amount of the composition is applied during and after bone distraction.

The present invention also provides methods of accelerating bone union following bone distraction. In some embodiments, a method for accelerating bone union following bone distraction comprises providing a composition comprising a PDGF solution disposed in a biocompatible matrix and applying an effective amount of the composition to at least one site of bone distraction.

The present invention additionally provides methods of performing osteodistraction procedures. In some embodiments, a method of performing an osteodistraction procedure comprises (a) partitioning a bone into a first bone segment and a second bone segment, (b) moving at least one of the first and second bone segments to produce a space between the first and second bone segments, and (c) stimulating osteogenesis in the space, wherein stimulating osteogenesis comprises providing a composition comprising a PDGF solution disposed in a biocompatible matrix and at least partially disposing an effective amount of the composition in the space. In some embodiments, steps (b) and (c) can be repeated as many times as necessary to lengthen the bone any desired amount.

In some embodiments of methods of the present invention, applying the composition comprises injecting the composition in a site of bone distraction. In some embodiments, injecting comprises percutaneous injection of the composition in the distraction site. In another embodiment, the composition is injected into an open or surgically exposed site of bone distraction. In a further embodiment, applying the composition comprises disposing (e.g. spreading) the composition in a site of bone distraction with a spatula or other device.

In various embodiments, the composition can be injected into the implantation site through e.g. a 10, 11, 12, 13, 14, 15, 16, 17, 18, 19, or 20 gauge needle.

In some embodiments of methods of the present invention, the biocompatible matrix comprising a bone scaffolding material. In some embodiments, the biocompatible matrix comprises a bone scaffolding material and a biocompatible binder.

In some embodiments, a composition of the present invention is applied to at least one site of bone distraction during the distraction phase of an osteodistraction procedure. In other embodiments, a composition of the present invention is applied to at least one site of bone distraction during the consolidation phase following bone distraction. In a further embodiment, a composition of the present invention is applied to at least one site of bone distraction during the distraction and consolidation phases.

In various embodiments, the bone may be lengthened a total of at least about 1 mm, at least about 2 mm, at least about 3 mm, at least about 4 mm, at least about 5 mm, at least about 6 mm, at least about 8 mm, at least about 10 mm, at least about 12 mm, at least about 15 mm, at least about 20 mm, at least about 25 mm, at least about 30 mm, at least about 35 mm, at least about 50 mm, at least about 75 mm, at least about 100 mm, at least about 125 mm, at least about 150 mm, at least about 175 mm, at least about 200 mm. In various embodiments, the first and second bone segments are separated by at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm per distraction step (e.g. during step (b) above). In some embodiments, the first and second bone segments are separated by about 0.5 mm to about 1.5 mm per distraction step. In some embodiments, the first and second bone segments are separated by about 0.8 mm to about 1.2 mm per distraction step. In some embodiments, the first and second bone segments are separated by about 1 mm per distraction step.

In some embodiments of the methods of the invention, the composition is applied to the distraction site once. In various embodiments, the composition is applied to the distraction site at least twice, at least three times, at least four times, at least five times, at least six times, at least eight times, at least ten times during the distraction and/or consolidation phases. In various embodiments, the composition may be administered to the distraction site more than once daily, daily, every other day, every third day, every fourth day, every fifth day, every six day, every week, or less than once per week during the distraction and/or consolidation phases.

In various embodiments, there is a significant increase in bone volume ($mm^3$) and/or bone volume fraction (BV/TV) in the new tissue within about 1 week, within about 2 weeks, within about 3 weeks, within about 4 weeks, within about 5 weeks, within about 6 weeks, within about 7 weeks, within about 8 weeks, within about 9 weeks, or within about 10 weeks of beginning dosing with the composition, as compared with untreated and matrix controls. In various embodiments, there is a significant increase in bone volume ($mm^3$) and/or bone volume fraction (BV/TV) in the new tissue within about 1 week, within about 2 weeks, within about 3 weeks, within about 4 weeks, within about 5 weeks, within about 6 weeks, within about 7 weeks, within about 8 weeks, within about 9 weeks, or within about 10 weeks of cessation of dosing with the composition, as compared with untreated and matrix controls.

As provided herein, osteodistraction procedures, according to embodiments of the present invention, comprise those used in the treatment of bilateral mandibular hypoplasia, hemifacial microsomia, congenital short femur, fibular hemimelia, hemiatrophy, achondroplasia, neurofibromatosis, bow legs, growth plate fractures, bone defects, craniofacial applications, osteomyelitis, septic arthritis, and poliomyelitis.

In some embodiments, a methods of the present invention further comprise providing at least one pharmaceutical composition in addition to the composition comprising a PDGF solution disposed in a biocompatible matrix and administering the at least one pharmaceutical composition locally and/or systemically. The at least one pharmaceutical composition, in some embodiments, comprises vitamins, such as vitamin $D_3$, calcium supplements, or any osteoclast inhibitor known to one of skill in the art, including bisphosphonates. In some embodiments, the at least one pharmaceutical composition is administered locally. In such embodiments, the at least one pharmaceutical composition can be incorporated into the biocompatible matrix or otherwise disposed in and around a site of bone distraction. In other embodiments, the at least one pharmaceutical composition is administered systemically to a patient. In some embodiments, for example, the at least one pharmaceutical composition is administered orally to a patient. In another embodiment, the at least one pharmaceutical composition is administered intravenously to a patient.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Preparation of a Composition Comprising a Solution of PDGF and a Biocompatible Matrix A composition comprising a solution of PDGF and a biocompatible matrix was prepared according to the following procedure.

A pre-weighed block of biocompatible matrix comprising β-TCP and collagen was obtained. The β-TCP comprised β-TCP particles having an average size ranging from about 100 µm to about 300 µm. The β-TCP particles were formulated with about 20 weight percent soluble Type I bovine collagen binder. Such a β-TCP/collagen biocompatible matrix can be commercially obtained from Kensey Nash (Exton, Pa.).

A solution comprising rhPDGF-BB was obtained. rhPDGF-BB is commercially available from Novartis Corporation at a stock concentration of 10 mg/ml (i.e., Lot # QA2217) in a sodium acetate buffer. The rhPDGF-BB is produced in a yeast expression system by Novartis Corporation and is derived from the same production facility as the rhPDGF-BB that is utilized in the products REGRANEX, (Johnson &Johnson) and GEM 21S (BioMimetic Therapeutics) which has been approved for human use by the United States Food and Drug Administration. This rhPDGF-BB is also approved for human use in the European Union and Canada. The rhPDGF-BB solution was diluted to 0.3 mg/ml in the sodium acetate buffer. The rhPDGF-BB solution can be diluted to any desired concentration according to embodiments of the present invention.

A ratio of about 3 ml of rhPDGF-BB solution to about 1 g dry weight of the β-TCP/collagen biocompatible matrix was used to produce the composition. The rhPDGF-BB solution was expelled on the biocompatible matrix with a syringe, and the resulting composition was blended and molded into a thin strand for insertion into a syringe for injection into a site of bone distraction.

Example 2

Preparation of a Composition Comprising a Solution of PDGF and a Biocompatible Matrix A composition comprising a PDGF solution disposed in a biocompatible matrix was prepared according to the following procedure.

A dry matrix of soluble bovine collagen weighing about 50 mg was obtained from Kensey Nash of Exton, Pa. The collagen matrix was added to a 1.5 ml microfuge test tube. 1.0 ml of a rhPDGF-BB solution in 20 mM sodium acetate buffer (pH 6.0) was added to the test tube containing the collagen matrix. The concentration of the rhPDGF-BB buffer solution was 0.3 mg/ml rhPDGF-BB. However, any desired concentration of rhPDGF-BB can be used. The collagen matrix soaked in the rhPDGF-BB buffer solution for about 10 minutes. After 10 minutes, the collagen matrix was removed from the test tube, inverted, and replaced in the test tube to assist in the hydration procedure. The collagen matrix was left in the test tube containing the rhPDGF-BB solution for an additional five minutes.

The hydrated collagen matrix and any remaining rhPDGF-BB solution in the test tube were placed in a sterile Petri dish. The hydrated collagen matrix and any remaining rhPDGF-BB solution was mixed with a sterile spatula to complete the hydration procedure. The hydrated collagen matrix was disposed in a first 3 ml syringe. Once in the first syringe, the hydrated collagen matrix was extruded into a second 3 ml syringe. The hydrated collagen matrix was subsequently extruded back into the first 3 ml syringe. The back and forth extrusion of the hydrated collagen matrix between the first and second syringes was performed 3 times to convert the hydrated collagen matrix into a flowable putty. Extrusion between the first and second syringes occurred through the open bores of the syringes with no needles attached.

After three cycles, a 16 gauge needle was added to the 3 ml syringe containing the hydrated collagen matrix, and the hydrated collagen matrix was extruded through the 16 gauge needle. The hydrated collagen matrix was subsequently extruded through a 20 gauge needle and loaded in to a 1 ml syringe for disposition at a site of bone distraction.

Example 3

Method of Performing an Osteodistraction Procedure 83 male Sprague Dawley rats (age about 6 months old, weight 400-500 g) were randomly divided into five treatment groups as provided in Table 1. Each rat underwent a unilateral mid-diaphyseal femoral lengthening (See Moore et al. *J. Orthop. Res.* 2003, 21:489-496). A custom, distractable four-pin monolateral fixator was applied to the right femur, followed by a periosteal-sparing mid-diaphyseal corticotomy to allow femoral lengthening. The wounds were closed in layers and the animals were returned to their cages and allowed unrestricted weight bearing. Following a seven day latency period, the femurs were lengthened 0.17 mm two times per day for 21 days, for a total lengthening of 7 mm.

TABLE 1

Treatment Strategy

| Treatment Groups | Number of Animals |
|---|---|
| 1) Buffer (0.2M sodium acetate) | 17 |
| 2) Injectable Collagen-Buffer (0.2M sodium acetate) | 16 |
| 3) Injectable Collagen-/PDGF (0.1 mg/ml PDGF) | 16 |
| 4) Injectable Collagen-/PDGF (0.3 mg/ml PDGF) | 17 |
| 5) Injectable Collagen-/PDGF (1.0 mg/ml PDGF) | 17 |
| Total | 83 | rhPDGF-BB solution or buffer was mixed with injectable, soluble bovine collagen in the concentrations delineated in Table 1. The soluble bovine collagen was obtained from Kensey Nash of Exton, Pa. and combined with the PDGF solution or sodium acetate buffer according to the procedure in Example 2.

On post-operative days 7, 14, 21, and 28, as set forth in the treatment and data acquisition scheme of Table 2, 50 µl of the assigned composition was injected in to the distraction gap of each animal in each treatment group. Administering 50 μl of the assigned composition resulted in the animals of Group 3 receiving 5 μg of rhPDGF-BB while the animals of Groups 4 and 5 received 15 μg and 50 μg of rhPDGF-BB respectively. Healing was followed every two weeks with radiographs taken with a high-resolution cabinet x-ray system (Faxitron MX 20 X-Ray, Faxitron X-Ray Corporation, Wheeling, Ill.).

TABLE 2

Treatment and Data Acquisition Scheme for All Groups

| | Day | | | | | | | | |
|---|---|---|---|---|---|---|---|---|---|
| | 1 | 7* | 14* | 21* | 28* | 35 | 42 | 49 | 56 | 63 |
| Injection: | ↑ | ↑ | ↑ | ↑ | | | | | |
| Faxitron X-ray | ↑ | ↑ | ↑ | ↑ | | ↑ | | ↑ | ↑ |
| μCT & Histology (n = 3/pt) | | | | | | ↑ | ↑ | ↑ | ↑ | ↑ |

*Distraction Phase

Animals (n=3) from each group were humanely sacrificed on post-operative days 35, 42, 49, 56, and 63. At sacrifice, the femurs were removed en bloc and placed in formalin. High-resolution 3-D images (16 μm isometric voxel size) were generated of a 16.5 mm region at the mid-diaphysis via micro-computed tomography (μCT40, Scanco Medical AG, Bassersdorf, CH). The original scanned images were segmented using a low-pass noise reducing filter ($\sigma=1$, support=1.0) and fixed threshold (316), and volume renderings were generated for visualization. New bone formation (BV) and bone volume fraction in the callus (BV/TV) were then calculated from a 6.4 mm (400-slice) segment centered in the distraction gap using the scanner system's built-in image processing software. Union was assessed by inspection of the volume renderings for bone bridging.

All data was analyzed using SAS® version 9.1.3 (SAS Institute, Inc., Cary, N.C.). Post hoc comparisons were performed using the Holm test, with alpha maintained ≦0.05. Prior to analysis, the BV data was logarithmically transformed to reduce positive skewness (Shapiro-Wilk p=0.28 after transform). Afterwards geometric means were back-translated for presentation.

The radiographs revealed new bone formation within the distraction gap in each of Groups 3-5 receiving a rhPDGF-BB-collagen composition. On day 28, new bone formation in control Groups 1 and 2 ranked significantly lower than new bone formation in Groups 3-5. Moreover, new bone formation in Group 4 (0.3 mg/ml rhPDGF-BB) ranked significantly higher than new bone formation in Group 5 (1.0 mg/ml rhPDGF-BB) and control Groups 1 and 2 (p<0.05 for all). On day 42, Group 4 (0.3 mg/ml rhPDGF-BB) ranked significantly higher in new bone formation than control Groups 1 and 2 (p<0.05).

Figure 2:
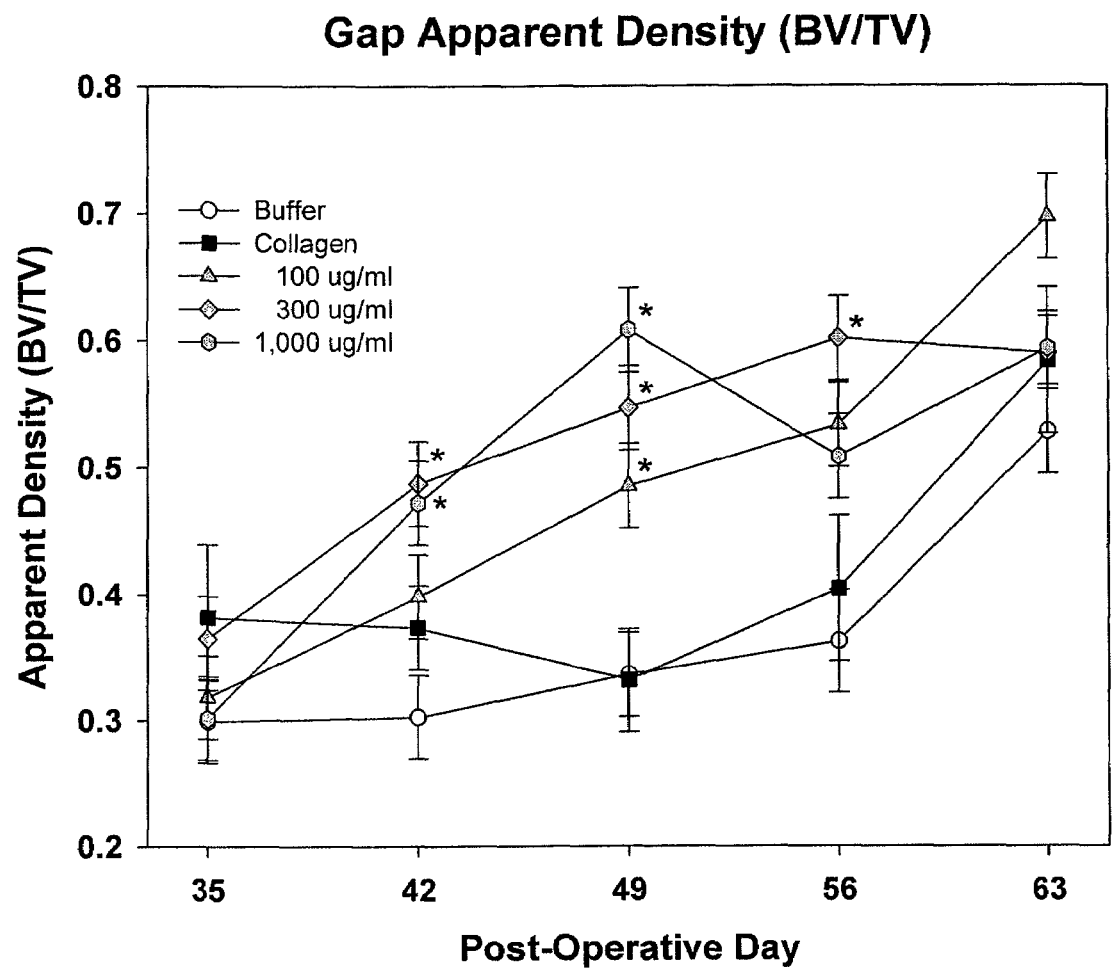
FIG. 2 illustrates fraction of new bone formation in a distraction procedure as a function of composition administered and healing time according to one embodiment of the present invention.

Mixed linear analysis of the BV and BV/TV data revealed statistically significant differences between control Groups 1 and 2 and Groups 3-5 (p<0.0001 for both BV and BV/TV) at various sacrifice time points. FIGS. 1 and 2 illustrate BV and BV/TV values for Groups 1-5 at each sacrifice time point. New bone formation was lowest in control Groups 1 and 2, which were not significantly different from one another at any time point. BV in Group 3 (0.1 mg/ml rhPDGF-BB) was greater than that in control Groups 1 and 2 on day 56 (p<0.05), and BV in Group 5 (1.0 mg/ml rhPDGF-BB) was greater than that in control Groups 1 and 2 on days 42 and 49 (p<0.05 for both). BV in Group 4 (0.3 mg/ml rhPDGF-BB) was greater than that in control Groups 1 and 2 on days 42, 49 and 56 (p=0.0002, p=0.0002 and p<0.0001, respectively).

Moreover, BV/TV in Group 3 (0.1 mg/ml rhPDGF-BB) was greater than that in control Groups 1 and 2 on day 49 (p=0.0009). BV/TV in Group 5 (1.0 mg/ml rhPDGF-BB) was greater than that in control Groups 1 and 2 on days 42 and 49 (p=0.0019 and p<0.0001, respectively), and BV/TV in Group 4 (0.3 mg/ml rhPDGF-BB) was greater than that in control Groups 1 and 2 on days 42, 49 and 56 (p=0.0007, p<0.0001 and p<0.0001, respectively).

Inspection of the μCT images suggested there was a general increase in the rate of bone bridging in Groups 3-5 receiving a rhPDGF-BB composition. As provided in Table 3, the union rate of the animals in Groups 3-5 at the time of sacrifice was significantly greater than that of the combined controls (40.3% vs. 4.55%, respectively, p=0.0127)

TABLE 3

μCT Assessed Bone Union

| Sacrifice Time point (days) | Treatment Group | | | | |
|---|---|---|---|---|---|
| | Acetate Buffer | Acetate + Collagen | Acetate + Collagen + 0.1 mg/mL rhPDGF-BB | Acetate + Collagen + 0.3 mg/mL | Acetate + Collagen + 1.0 mg/mL |
| 35 | 0/3 | 0/1 | 0/3 | 0/3 | 0/3 |
| 42 | 0/3 | 0/3 | 1/3 | 2/3 | 1/3 |
| 49 | 0/3 | 0/2 | 1/3 | 1/3 | 1/3 |
| 56 | 0/2 | 0/1 | 2/3 | 2/3 | 0/3 |
| 63 | 0/3 | 1/1 | 2/3 | 4/4 | 2/4 |
| Total | 1/22 (4.55%) | | 19/47 (40.43%) | | |

From the results of the present study, the administration of compositions comprising rhPDGF-BB to distraction sites significantly increases new bone formation during the distraction procedure and accelerates bone union.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A method of stimulating osteogenesis in a bone distraction procedure, wherein the osteogenesis stimulation consists of: applying an effective amount of a composition consisting of a platelet-derived growth factor (PDGF) solution disposed in a biocompatible matrix to at least one site of bone distraction, wherein the PDGF solution consists of PDGF in a buffer, wherein the PDGF is present in the solution in a concentration ranging from about 0.01 mg/ml to about 10 mg/ml, wherein the biocompatible matrix: (i) consists of a porous calcium phosphate, (ii) consists of collagen and a porous calcium phosphate, (iii) consists of an allograft, or (iv) consists of collagen and an allograft, wherein the calcium phosphate or allograft comprises interconnected pores, and wherein the calcium phosphate or allograft consists of particles in a range of about 100 to about 5000 microns in size.

2. The method of claim 1, wherein the composition is applied during the distraction phase of the osteodistraction procedure.

3. The method of claim 1, wherein the composition is applied during the consolidation phase of the osteodistraction procedure.

4. The method of claim 1, wherein the composition is applied during the distraction and consolidation phases of the osteodistraction procedure.

5. The method of claim 1, wherein the method comprises accelerating bone consolidation following bone distraction.

6. The method of claim 1, wherein the composition is applied to the site at least twice.

7. The method of claim 1, wherein the biocompatible matrix consists of a porous calcium phosphate.

8. The method of claim 7, wherein the calcium phosphate comprises β-TCP.

9. The method of claim 7, wherein the calcium phosphate consists of particles in a range of about 250 microns to about 1000 microns in size.

10. The method of claim 7, wherein the calcium phosphate has a porosity greater than about 40%.

11. The method of claim 7, wherein the calcium phosphate consists of particles in a range of about 1000 microns to about 3000 microns in size.

12. The method of claim 11, wherein the calcium phosphate consists of particles in a range of about 100 microns to about 300 microns in size.

13. The method of claim 7, wherein the biocompatible matrix is resorbable such that at least about 80% of the calcium phosphate is resorbed within about one year of being implanted.

14. The method of claim 7, wherein the calcium phosphate is capable of absorbing an amount of the PDGF solution that is equal to at least about 25% of the weight of the calcium phosphate.

15. The method of claim 1, wherein the biocompatible matrix consists of a porous calcium phosphate and collagen.

16. The method of claim 7, wherein the PDGF is present in the solution at a concentration of about 0.1 mg/ml to about 1.0 mg/ml.

17. The method of claim 16, wherein the PDGF is present in the solution at a concentration of about 0.3 mg/ml.

18. The method of claim 7, wherein the buffer is sodium acetate.

19. The method of claim 7, wherein the calcium phosphate has a porosity that facilitates cell migration into the composition.

20. The method of claim 15, wherein the biocompatible matrix consists of collagen and β-TCP in a ratio of about 20:80.

21. The method of claim 1, wherein the composition is injectable.

22. A method of performing an osteodistraction procedure comprising:
  (a) partitioning a bone into a first bone segment and a second bone segment;
  (b) moving at least one of the first and second bone segments to form a space between the first and second bone segments; and
  (c) stimulating osteogenesis in the space,
  wherein stimulating osteogenesis consists of applying an effective amount of a composition consisting of a PDGF solution disposed in a biocompatible matrix to the space;
  wherein the PDGF solution consists of PDGF in a buffer,
  wherein the PDGF is present in the solution in a concentration ranging from about 0.01 mg/ml to about 10 mg/ml,
  wherein the biocompatible matrix: (i) consists of a porous calcium phosphate, (ii) consists of collagen and a porous calcium phosphate, (iii) consists of an allograft, or (iv) consists of collagen and an allograft,
  wherein the calcium phosphate or allograft comprises interconnected pores, and
  wherein the calcium phosphate or allograft consists of particles in a range of about 100 to about 5000 microns in size.

23. The method of claim 22, further comprising repeating steps (b) and (c) a number of times necessary to lengthen the bone a desired amount.

24. The method of claim 9, wherein the calcium phosphate consists of β-TCP, wherein the PDGF is present in the solution at a concentration of about 0.1 mg/ml to about 1.0 mg/ml, and wherein the calcium phosphate has a porosity greater than about 40%.

25. The method of claim 11, wherein the calcium phosphate consists of β-TCP, wherein the PDGF is present in the solution at a concentration of about 0.1 mg/ml to about 1.0 mg/ml, and wherein the calcium phosphate has a porosity greater than about 40%.

26. The method of claim 12, wherein the calcium phosphate consists of β-TCP, wherein the PDGF is present in the solution at a concentration of about 0.1 mg/ml to about 1.0 mg/ml, and wherein the calcium phosphate has a porosity greater than about 40%.

27. The method of claim 15, wherein the calcium phosphate comprises β-TCP.

28. The method of claim 15, wherein the calcium phosphate has a porosity greater than about 40%.

29. The method of claim 15, wherein the calcium phosphate consists of particles in a range of about 250 microns to about 1000 microns in size.

30. The method of claim 15, wherein the calcium phosphate consists of particles in a range of about 1000 microns to about 3000 microns in size.

31. The method of claim 15, wherein the calcium phosphate consists of particles in a range of about 100 microns to about 300 microns in size.

32. The method of claim 15, wherein the biocompatible matrix is resorbable such that at least about 80% of the calcium phosphate is resorbed within about one year of being implanted.

33. The method of claim 15, wherein the calcium phosphate is capable of absorbing an amount of the PDGF solution that is equal to at least about 25% of the weight of the calcium phosphate.

34. The method of claim 15, wherein the PDGF is present in the solution at a concentration of about 0.1 mg/ml to about 1.0 mg/ml.

35. The method of claim 15, wherein the PDGF is present in the solution at a concentration of about 0.3 mg/ml.

36. The method of claim 15, wherein the buffer is sodium acetate.

37. The method of claim 15, wherein the calcium phosphate has a porosity that facilitates cell migration into the composition.

38. The method of claim 29, wherein the calcium phosphate consists of β-TCP, wherein the PDGF comprises PDGF-BB, wherein the PDGF is present in the solution at a concentration of about 0.1 mg/ml to about 1.0 mg/ml, and wherein the calcium phosphate has a porosity greater than about 40%.

39. The method of claim 38, wherein the biocompatible matrix consists of collagen and β-TCP in a ratio of about 20:80.

40. The method of claim 30, wherein the calcium phosphate consists of β-TCP, wherein the PDGF comprises PDGF-BB, wherein the PDGF is present in the solution at a concentration of about 0.1 mg/ml to about 1.0 mg/ml, and wherein the calcium phosphate has a porosity greater than about 40%.

41. The method of claim 40, wherein the biocompatible matrix consists of collagen and β-TCP in a ratio of about 20:80.

42. The method of claim 31, wherein the calcium phosphate consists of β-TCP, wherein the PDGF comprises PDGF-BB, wherein the PDGF is present in the solution at a concentration of about 0.1 mg/ml to about 1.0 mg/ml, and wherein the calcium phosphate has a porosity greater than about 40%.

43. The method of claim 42, wherein the biocompatible matrix consists of collagen and β-TCP in a ratio of about 20:80.

44. The method of claim 15, wherein the composition is injectable.

45. The method of claim 1, wherein the composition is molded to the contours of the site.

46. The method of claim 1, wherein the composition is spread over at least one bone surface.

* * * * *